United States Patent
Mclaughlin et al.

(10) Patent No.: US 12,201,726 B2
(45) Date of Patent: *Jan. 21, 2025

(54) PRESERVING FUNCTIONALLY-COATED API PARTICLES PRODUCED BY SOLVENTLESS MIXING PROCESSES IN AQUEOUS SUSPENSION

(71) Applicant: Catalent U.K. Swindon Zydis Limited, Swindon (GB)

(72) Inventors: Rosaleen Mclaughlin, Swindon (GB); Adam Parker, Swindon (GB); Jonathon Whitehouse, Swindon (GB)

(73) Assignee: Catalent U.K. Swindon Zydis Limited, Swindon (GB)

( * ) Notice: Subject to any disclaimer, the term of this patent is extended or adjusted under 35 U.S.C. 154(b) by 107 days.

This patent is subject to a terminal disclaimer.

(21) Appl. No.: 17/529,827

(22) Filed: Nov. 18, 2021

(65) Prior Publication Data

US 2022/0071907 A1 Mar. 10, 2022

Related U.S. Application Data

(63) Continuation of application No. 16/797,934, filed on Feb. 21, 2020, now Pat. No. 11,185,508.

(Continued)

(51) Int. Cl.
*A61K 9/50* (2006.01)
*A61K 9/16* (2006.01)
(Continued)

(52) U.S. Cl.
CPC .......... *A61K 9/1635* (2013.01); *A61K 9/1623* (2013.01); *A61K 9/1652* (2013.01);
(Continued)

(58) Field of Classification Search
None
See application file for complete search history.

(56) References Cited

U.S. PATENT DOCUMENTS

| 4,305,502 A | 12/1981 | Gregory et al. |
| 4,371,516 A | 2/1983 | Gregory et al. |

(Continued)

FOREIGN PATENT DOCUMENTS

| CA | 2398288 A1 | 8/2001 |
| CA | 2512988 A1 | 8/2004 |

(Continued)

OTHER PUBLICATIONS

Evonik-Glenn Corp Aerosil® R972 ([online] retrieved on May 16, 2023 from: https://glenncorp.com/shop/aerosil-r-972/; 1 page) (Year: 2023).*

(Continued)

*Primary Examiner* — Ernst V Arnold
(74) *Attorney, Agent, or Firm* — Morrison & Foerster LLP

(57) ABSTRACT

Provided are pharmaceutical compositions and methods for preparing pharmaceutical compositions that preserve the coating of coated API particles in a pharmaceutical suspension. Pharmaceutical compositions include coated active pharmaceutical ingredient (API) particles comprising: an API particle; a first coating comprising one or more deformed components coating the API particle; a second coating comprising silica surrounding and/or partially or fully embedded into the first coating, a matrix former, and a structure former.

17 Claims, 8 Drawing Sheets

Related U.S. Application Data

(60) Provisional application No. 62/809,287, filed on Feb. 22, 2019.

(51) Int. Cl.
  *A61K 9/28* (2006.01)
  *A61K 47/02* (2006.01)
  *A61K 47/44* (2017.01)

(52) U.S. Cl.
  CPC .......... *A61K 9/1658* (2013.01); *A61K 9/1682* (2013.01); *A61K 9/2813* (2013.01); *A61K 9/288* (2013.01)

(56) References Cited

U.S. PATENT DOCUMENTS

| | | | |
|---|---|---|---|
| 4,758,598 | A | 7/1988 | Gregory |
| 5,008,117 | A | 4/1991 | Calanchi et al. |
| 5,320,848 | A | 6/1994 | Geyer |
| 5,558,880 | A | 9/1996 | Gole et al. |
| 5,976,577 | A | 11/1999 | Green et al. |
| 6,214,386 | B1 | 4/2001 | Santus |
| 6,413,549 | B2 | 7/2002 | Green et al. |
| 6,509,040 | B1 | 1/2003 | Murray et al. |
| 6,709,669 | B1 | 3/2004 | Murray et al. |
| 6,951,657 | B1 | 10/2005 | Zuccarelli |
| 9,107,851 | B2 | 8/2015 | Dave et al. |
| 11,026,892 | B2 * | 6/2021 | McLaughlin ........ A61K 9/1658 |
| 11,077,067 | B2 * | 8/2021 | McLaughlin .......... A61K 9/501 |
| 11,141,380 | B2 * | 10/2021 | McLaughlin ........ A61K 9/1658 |
| 11,166,919 | B2 * | 11/2021 | McLaughlin ............ A61K 9/19 |
| 11,185,508 | B2 * | 11/2021 | McLaughlin .......... A61K 9/501 |
| 2003/0185096 | A1 | 10/2003 | Hollstein et al. |
| 2003/0195179 | A1 | 10/2003 | Sawa |
| 2004/0137061 | A1 | 7/2004 | Ishibashi et al. |
| 2004/0170686 | A1 | 9/2004 | Fredrickson et al. |
| 2004/0265373 | A1 | 12/2004 | Wynn et al. |
| 2007/0148099 | A1 | 6/2007 | Burke et al. |
| 2007/0292508 | A1 | 12/2007 | Szamosi et al. |
| 2008/0075825 | A1 | 3/2008 | Fuisz et al. |
| 2008/0096979 | A1 | 4/2008 | Pilgaonkar |
| 2008/0113021 | A1 | 5/2008 | Shen |
| 2008/0311201 | A1 | 12/2008 | Der-Yang et al. |
| 2008/0317853 | A1 | 12/2008 | Kashid et al. |
| 2009/0062241 | A1 | 3/2009 | Bauer |
| 2009/0148524 | A1 | 6/2009 | Higuchi et al. |
| 2011/0229573 | A1 | 9/2011 | Tian |
| 2013/0071481 | A1 * | 3/2013 | Ichikawa ............. A61K 9/5026 424/494 |
| 2014/0105936 | A1 | 4/2014 | Limonov et al. |
| 2014/0106059 | A1 | 4/2014 | Dave et al. |
| 2016/0361335 | A1 | 12/2016 | Jacob et al. |
| 2020/0268667 | A1 | 8/2020 | McLaughlin et al. |
| 2020/0268668 | A1 | 8/2020 | McLaughlin |
| 2020/0268676 | A1 | 8/2020 | McLaughlin |
| 2020/0268677 | A1 | 8/2020 | McLaughlin et al. |
| 2023/0390205 | A1 | 12/2023 | McLaughlin et al. |

FOREIGN PATENT DOCUMENTS

| | | | |
|---|---|---|---|
| CN | 102300558 | A | 12/2011 |
| CN | 102579390 | A | 7/2012 |
| CN | 103169655 | A | 6/2013 |
| CN | 104853751 | A | 8/2015 |
| EP | 0 636 365 | * | 2/1995 ............... A61K 9/20 |
| EP | 0636365 | A1 | 2/1995 |
| EP | 1405635 | A1 | 4/2004 |
| EP | 1621186 | A1 | 2/2006 |
| GB | 211423 | | 2/1924 |
| GB | 1548022 | A | 7/1979 |
| JP | H9-511256 | A | 11/1997 |
| JP | 2002-012557 | A | 1/2002 |
| JP | 2003-055197 | A | 2/2003 |
| JP | 2003-525223 | A | 8/2003 |
| JP | 2007-525413 | A | 9/2007 |
| JP | 2008-508255 | A | 3/2008 |
| JP | 2008-517979 | A | 5/2008 |
| JP | 2008-526827 | A | 7/2008 |
| JP | 2015-533162 | A | 11/2015 |
| JP | 2017-532331 | A | 11/2017 |
| TW | 512167 | B | 12/2002 |
| WO | 92/22369 | A1 | 12/1992 |
| WO | 01/54683 | A1 | 8/2001 |
| WO | 02/47607 | A2 | 6/2002 |
| WO | 2004/066925 | A2 | 8/2004 |
| WO | 2006/045830 | A1 | 5/2006 |
| WO | 2006/072832 | A1 | 7/2006 |
| WO | 2008/036299 | A2 | 3/2008 |
| WO | 2009/108775 | A2 | 9/2009 |
| WO | 2011/063531 | A1 | 6/2011 |
| WO | 2013/024373 | A1 | 2/2013 |
| WO | 2013/183062 | A2 | 12/2013 |
| WO | WO-2014062444 | A1 * | 4/2014 ........... A61K 9/5042 |
| WO | 2017/080566 | A1 | 5/2017 |
| WO | 2020/169989 | A1 | 8/2020 |

OTHER PUBLICATIONS

Huang et al. (European Journal of Pharmaceutical Sciences 104 (2017) 344-355). (Year: 2017).*

Anonymous. (2014). "Safety Data Sheet Orange Tincture," located at <https://jmloveridge.com/wp-content/uploads/2018/06/Orange-Tincture-Version-06.pdf> retrieved on Mar. 24, 2022; 6 pages.

Deterre et al. (2014). "Classification of commercial bitter orange essential oils (*Citrus aurantium* L.), based on a combination of chemical and sensory analyses of specific odor markers," Journal of Essential Oil Research 26 (4): 254-262.

McLaughlin et al., U.S. Office Action dated Mar. 30, 2022, directed to U.S. Appl. No. 16/798,067; 20 pages.

First Office Action dated Nov. 3, 2022, directed to CN Application No. 202080015446.5; 22 pages.

Written Opinion dated Nov. 2, 2022, directed to SG Application No. 11202108659X; 8 pages.

Written Opinion dated Nov. 2, 2022, directed to SG Application No. 11202109104X; 7 pages.

McLaughlin et al., U.S. Office Action dated Aug. 23, 2022, directed to U.S. Appl. No. 16/798,067; 15 pages.

McLaughlin et al., U.S. Office Action dated Dec. 22, 2022, directed to U.S. Appl. No. 16/798,067; 14 pages.

Written Opinion dated Nov. 2, 2022, directed to SG Application No. 11202109022U; 8 pages.

Written Opinion dated Nov. 3, 2022, directed to SG Application No. 11202108690Y; 11 pages.

Examination Report dated Feb. 6, 2023, directed to GB Application No. 2002466.7; 4 pages.

Examination Report dated Feb. 8, 2023, directed to GB Application No. 2107172.5; 3 pages.

Examination Report dated Feb. 14, 2023, directed to GB Application No. 2002475.8; 3 pages.

McLaughlin et al., U.S. Office Action dated Feb. 6, 2023, directed to U.S. Appl. No. 17/307,638; 17 pages.

Office Action dated Feb. 22, 2023, directed to IN Application No. 202127042578; 5 pages.

Office Action dated Feb. 27, 2023, directed to EP Application No. 20708584.6; 5 pages.

Combined Search and Examination Report dated Apr. 28, 2020, directed to GB Application No. 2002466.7; 5 pages.

Combined Search and Examination Report dated Apr. 28, 2020, directed to GB Application No. 2002475.8; 7 pages.

Combined Search and Examination Report dated Apr. 28, 2020, directed to GB Application No. 2002479.0; 8 pages.

Combined Search and Examination Report dated Apr. 28, 2020, directed to GB Application No. 2002484.0; 7 pages.

Combined Search and Examination Report dated Nov. 22, 2021, directed to GB Application No. 2107177.4; 5 pages.

Combined Search and Examination Report dated Nov. 22, 2021, directed to GB Application No. 2107172.5; 4 pages.

(56) References Cited

OTHER PUBLICATIONS

Combined Search and Examination Report dated Nov. 22, 2021, directed to GB Application No. 2107174.1; 4 pages.
International Search Report and Written Opinion dated Nov. 5, 2021, directed to PCT/IB2021/056976; 15 pages.
International Search Report and Written Opinion mailed Apr. 17, 2020, directed to International Application No. PCT/GB2020/050419; 15 pages.
International Search Report and Written Opinion mailed Apr. 20, 2020, directed to International Application No. PCT/GB2020/050420; 13 pages.
International Search Report and Written Opinion mailed Apr. 21, 2020, directed to International Application No. PCT/GB2020/050422; 14 pages.
International Search Report and Written Opinion mailed Apr. 21, 2020, directed to International Application No. PCT/GB2020/050423; 14 pages.
McLaughlin et al., Office Action dated Apr. 12, 2021, directed to U.S. Appl. No. 16/797,927; 21 pages.
McLaughlin et al., Office Action dated Apr. 13, 2021, directed to U.S. Appl. No. 16/798,130; 29 pages.
McLaughlin et al., Office Action dated Dec. 7, 2020, directed to U.S. Appl. No. 17/008,318; 16 pages.
McLaughlin et al., Office Action dated Dec. 9, 2020, directed to U.S. Appl. No. 17/008,108; 22 pages.
McLaughlin et al., Office Action dated Feb. 10, 2021, directed to U.S. Appl. No. 16/797,934; 24 pages.
McLaughlin et al., Office Action dated May 12, 2021, directed to U.S. Appl. No. 16/797,934; 22 pages.
National Center for Biotechnology Information. (Apr. 28, 2006). "Compound Summary-Simethicone," located at https://pubchem.ncbi.nlm.nih.gov/compound/Simethicone (2 pages).
O'Connell (May 2005). "Sieve Use in the Pharmaceutical Industry," Pharmaceutical Technology Europe 17(5): 7 pages.
Syloid FG Silica (2015) "Syloid 244 FP silica: Formulation of viscous Simethicone in to chewable tablets," located at https://www.pharmaexcipients.com/wp-content/uploads/attachments/AP010_Syloid+244+FP-Formulation+of+Simethicone+into+chewable+tablets_Final.pdf?t=1458129627. (2 pages).
Zhou et al. (Aug. 2013). "Improving manufacturability of an ibuprofen powder blend by surface coating with silica nanoparticles," Powder Technology 249: 290-296.
McLaughlin et al., U.S. Office Action dated Jun. 8, 2023, directed to U.S. Appl. No. 17/390,331; 11 pages.
McLaughlin et al., U.S. Office Action dated May 15, 2023, directed to U.S. Appl. No. 17/387,803; 18 pages.
Office Action dated Jun. 1, 2023, directed to GB Application No. 2107172.5; 1 page.
Office Action dated May 2, 2023, directed to IN Application No. 202127042581; 6 pages.
Office Action dated May 22, 2023, directed to CN Application No. 202080015446.5; 8 pages.
Office Action dated May 31, 2023, directed to GB Application No. 2002466.7; 1 page.
Office Action dated May 31, 2023, directed to GB Application No. 2002475.8; 2 pages.
Office Action dated May 31, 2023, directed to IN Application No. 202127042580; 6 pages.
Andrews. (2017)."How to Extract Oil from Orange Peels," downloaded from URL https://web.archive.org/web/20170603094953/https://www.wikihow.com/Extract-Oil-from-Orange-Peels retrieved on May 24, 2023; 5 pages.
Andrews. (2018) "How to Extract Oil from the Skin of Oranges," downloaded from https://www.weekand.com/ healthy-living/article/extract-oil-skin-oranges-18009337.php retrieved on Jun. 14, 2023; 4 pages.
Anonymous. (2013). "Making Orange Tincture," downloaded from https://boozyblog.wordpress.com/2013/08/05/making-orange-tincture/ retrieved on Jun. 14, 2023; 7 pages.
Bourgou et al. (2012). "Changes of Peel Essential Oil Composition of Four Tunisian Citrus during Fruit Maturation," The Scientific World Journal; Article ID 528593; 10 pages.
Jabri Karoui et al. (2013). "Characterization of Bioactive Compounds in Tunisian Bitter Orange (*Citrus aurantium* L.) Peel and Juice and Determination of Their Antioxidant Activities," BioMed Research International; Article ID: 345415; 12 pages.
McLaughlin et al., U.S. Advisory Action dated Jun. 21, 2023, directed to U.S. Appl. No. 16/798,067; 5 pages.
McLaughlin et al., U.S. Office Action dated Aug. 29, 2023, directed to U.S. Appl. No. 16/798,067; 16 pages.
McLaughlin et al., U.S. Office Action dated Sep. 13, 2023, directed to U.S. Appl. No. 17/387,803; 10 pages.
Office Action dated Aug. 9, 2023, directed to MX Application No. MX/a/2021/009844; 5 pages.
Office Action dated Jul. 10, 2023, directed to RU Application No. 2021127592; 37 pages.
Office Action dated Jul. 11, 2023, directed to MX Application No. MX/a/2021/009845; 6 pages.
Office Action dated Jul. 12, 2023, directed to RU Application No. 2021127591; 25 pages.
Office Action dated Jul. 14, 2023, directed to RU Application No. 2021127588; 22 pages.
Office Action dated Jul. 18, 2023, directed to TW Application No. 109105762; 14 pages.
Office Action dated Jul. 26, 2023, directed to TW Application No. 109105759; 12 pages.
Office Action dated Jul. 28, 2023, directed to IN Application No. 202127042579; 8 pages.
Office Action dated Jun. 23, 2023, directed to MX Application No. MX/a/2021/009679; 6 pages.
Office Action dated Jun. 27, 2023, directed to MX Application No. MX/a/2021/009681; 6 pages.
Office Action dated Nov. 17, 2023, directed to MX Application No. MX/a/2021/009844; 6 pages.
Office Action dated Nov. 3, 2023, directed to TW Application No. 109105770; 8 pages.
Office Action dated Oct. 12, 2023, directed to MX Application No. MA/a/2021/009681; 9 pages.
Office Action dated Sep. 13, 2023, directed to MX Application No. MX/a/2021/009679; 10 pages.
Office Action dated Sep. 28, 2023, directed to PH Application No. 1/2021/552022; 4 pages.
Third Office Action dated Sep. 18, 2023, directed to CN Application No. 202080015446.5; 10 pages.
McLaughlin et al., U.S. Office Action dated Dec. 7, 2023, directed to U.S. Appl. No. 17/390,331; 6 pages.
Office Action dated Dec. 11, 2023, directed to RU Application No. 2021127590; 24 pages.
Office Action dated Dec. 6, 2023, directed to RU Application No. 2021127592; 17 pages.
Office Action dated Dec. 7, 2023, directed to RU Application No. 2021127591; 14 pages.
Extended European search report dated Dec. 18, 2023, directed to EP Application No. 23183926.7; 8 pages.
First Office Action dated Dec. 27, 2023, directed to CN Application No. 202080015572.0; 34 pages.
Notice of Reasons for Rejection dated Dec. 4, 2023, directed to JP Application No. 2021-549375; 11 pages.
Office Action dated Dec. 12, 2023, directed to RU Application No. 2021127588; 16 pages.
Office Action dated Nov. 1, 2023, directed MX Application No. MX/a/2021/009845; 11 pages.
Office Action dated Nov. 4, 2023, directed to CN Application No. 202080015635.2; 23 pages.
Office Action dated Nov. 7, 2023, directed to TW Application No. 109105773; 10 pages.
Office Action dated Nov. 8, 2023, directed to TW Application No. 109105762; 10 pages.
Office Action dated Nov. 9, 2023, directed to CN Application No. 202080015564.6; 28 pages.
Office Action dated Jul. 13, 2023, directed to RU Application No. 2021127590; 30 pages.

(56) References Cited

OTHER PUBLICATIONS

Chueshov et al. (2002). Industrial Drug Technology. vol. 2; pp. 352-355.
Pertsev et al. (1999). Pharmaceutical and biomedical aspects of drugs, vol. 1; pp. 253-254.
Bikiaris et al., (2007). "New Aspects in Sustained Drug Release Formulations," Recent Patents on Drug Delivery & Formulation 1(3): 201-213.
Extended European Search Report dated Jan. 23, 2024, directed to EP Application No. 23186234.3; 10 pages.
Extended European Search Report dated Jan. 31, 2024, directed to EP Application No. 23189317.3; 16 pages.
Gad, 2005. "Limonene," Encyclopedia of Toxicology (Second Edition), pp. 720-725.
Office Action dated Dec. 7, 2023, directed to TW Application No. 109105759; 8 pages.
Office Action dated Jan. 30, 2024, directed to MX Application No. MX/a/2021/009679; 9 pages.
Office Action dated Jan. 9, 2024, directed to JP Application No. 2021-549372; 9 pages.
Office Action dated Jan. 9, 2024, directed to JP Application No. 2021-549373; 12 pages.
Subsequent Substantive Examination Report dated Jan. 12, 2024, directed to EP Application No. Jan. 2021/552022; 4 pages.
McLaughlin et al., Office Action dated Mar. 7, 2024, directed to U.S. Appl. No. 16/795,067; 21 pages.
Office Action dated Apr. 18, 2024, directed to IL Application No. 285653; 4 pages.
Office Action dated Apr. 22, 2024, directed to MX Application No. MX/a/2021/009845; 5 pages.
Office Action dated Feb. 22, 2024, directed to MX Application No. MX/a/2021/009681; 8 pages.
Office Action dated Mar. 11, 2024, directed to JP Application No. 2021-549374; 11 pages.
Office Action dated Mar. 21, 2024, directed to IL Application No. 285640; 4 pages.
Office Action dated Mar. 27, 2024, directed to IL Application No. 285648; 4 pages.
Office Action dated Mar. 4, 2024, directed to IN Application No. 202127042580; 3 pages.
Office Action dated Mar. 5, 2024, directed to MX Application No. MX/a/2021/009844; 7 pages.
Office Action dated May 9, 2024, directed to MX Application No. MX/a/2021/2021009679; 10 pages.
Decision of Rejection dated Jul. 8, 2024, directed to JP Application No. 2021-549375; 7 pages.
McLaughlin et al., U.S. Office Action dated Jul. 17, 2024, directed to U.S. Appl. No. 16/798,067; 21 pages.
Office Action dated Aug. 13, 2024, directed to JP Application No. 2021-549374; 5 pages.
Office Action dated Aug. 27, 2024, directed to BR Application No. 112021016405-7; 5 pages.
Office Action dated Aug. 30, 2024, directed to CN Application No. 202080015564.6; 28 pages.
Office Action dated Jul. 26, 2024, directed to CN Application No. 202080015635.2; 14 pages.
Office Action dated Jun. 18, 2024, directed to MX Application No. MX/a/2021/009681; 11 pages.
Office Action dated May 6, 2024, directed to TW Application No. 109105773; 9 pages.
Office Action dated May 7, 2024, directed to CN Application No. 202180051278.X; 20 pages.
Office Action dated Oct. 1, 2024, directed to AU Application No. 2020223894; 3 pages.
Office Action dated Sep. 24, 2024, directed to AU Application No. 2020225818; 3 pages.
Office Action dated Sep. 26, 2024, directed to AU Application No. 2020225448; 4 pages.
Second Office Action dated Aug. 29, 2024, directed to CN Application No. 202080015572.0; 39 pages.

* cited by examiner

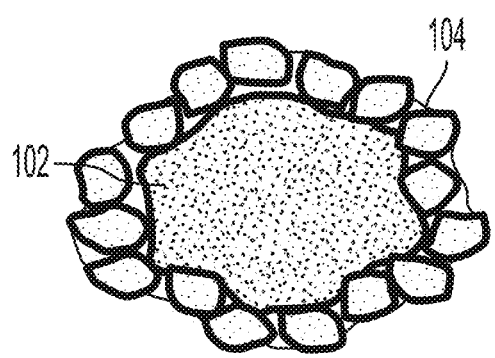 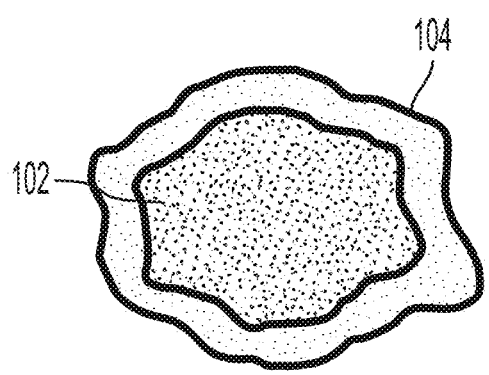
FIG. 1A  FIG. 1B
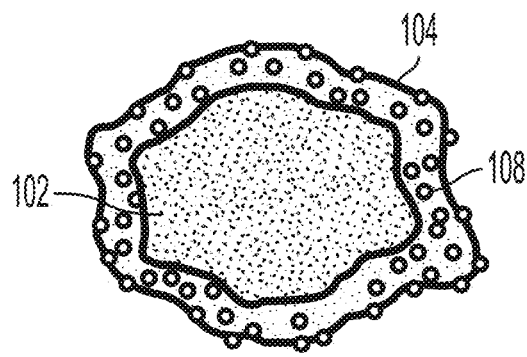
FIG. 1C
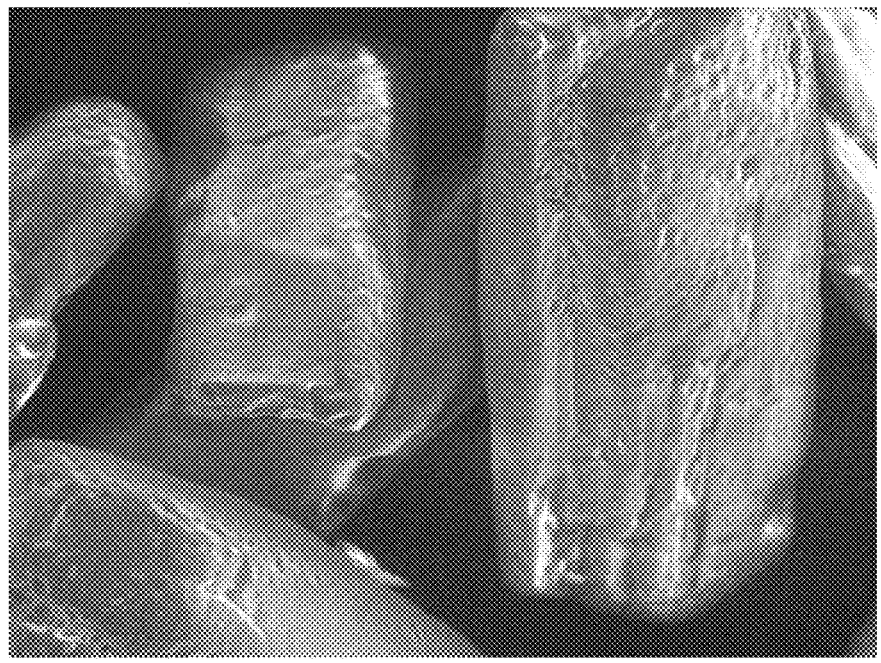
FIG. 2

PRESERVING FUNCTIONALLY-COATED API PARTICLES PRODUCED BY SOLVENTLESS MIXING PROCESSES IN AQUEOUS SUSPENSION

CROSS REFERENCE TO RELATED APPLICATIONS

This application is a continuation of U.S. application Ser. No. 16/797,934, filed Feb. 21, 2020, which claims the priority of U.S. Provisional Application No. 62/809,287, filed Feb. 22, 2019, the entire contents of each of which are incorporated herein by reference.

FIELD OF THE INVENTION

This relates to preserving functionally-coated active pharmaceutical ingredients (APIs) in a pharmaceutical suspension, and more particularly, to preserving the coating of functionally-coated APIs produced by solventless mixing processes and formulated to delay release of the API upon oral administration.

BACKGROUND OF THE INVENTION

Pharmaceutical compositions typically include both an active pharmaceutical ingredient (API) as well as one or more inactive ingredients. The API is biologically active and is designed to directly affect a patient's symptoms, diseases, disorders, and/or ailments. The inactive ingredient(s) of a pharmaceutical composition, on the other hand, are pharmaceutically inert and can be used for various purposes including, but not limited to, improving long-term stabilization, filling or diluting a solid formulation, facilitating drug absorption, modifying viscosity of liquid formulations, enhancing solubility and/or aiding the manufacture of the pharmaceutical composition.

In addition, some inactive ingredients may be used to mask the taste of the API. Many APIs are known to exhibit unpleasant organoleptic properties if allowed to dissolve in the oral cavity, such as bitter taste, burning sensation, and numbing. For example, some orally-administered pharmaceutical compositions are designed to disperse in the mouth to enable administration without water. These types of orally-administered pharmaceutical compositions may be targeted to pediatric patients, geriatric patients, animal patients, and/or other types of patients that may have difficulties swallowing. For these types of orally-administered pharmaceutical compositions, an inactive ingredient may be used to form a "functional coating" to mask the taste of the API.

An inactive ingredient may be used to mask the taste of the API by wet coating or dry coating the API to produce a functional coating surrounding the API such that it prevents API release in the oral cavity. In wet particle coating, inactive ingredients (polymers and additives) are dissolved or dispersed in solvent or water to form a suspension or solution. This suspension or solution may be sprayed onto the surface of the API particles to form a coating film upon evaporation of the solvent or water. Examples of technologies for wet particle coating include microencapsulation, fluid bed coating, solvent evaporation, spray drying, pan coating etc. In dry particle coating (also referred to as solventless coating), API particles are mechanically coated with fine particles of inactive ingredients (polymers and additives) to form particle composites. Examples of dry particle coating include hot melt coating, supercritical coating, impaction coating, electrostatic coating etc. API particles coated with a taste-masking inactive ingredient may provide a more pleasant experience for a patient having difficulties swallowing or having a sensitivity to taste that would otherwise lead to a negative patient experience and poor compliance in particular for pharmaceutical compositions that dissolve or disintegrate in the mouth.

For example, a dry, solventless mixing method may use high energy vibrations or acoustic resonance to mix the API with the inactive ingredient(s). Further, coating an API with a functional coating may temporarily delay the release of the API in a patient's mouth during dispersion of the pharmaceutical composition, yet still allow at least 90% of the API that would be released without the coating to be released from the functionally-coated API within a suitable amount of time for absorption. Coating the API in a taste-masking inactive ingredient allows the dissolution rate of the functionally-coated API to be controlled such that a majority of the API is not released until after the functionally-coated API has passed into a patient's stomach.

SUMMARY OF THE INVENTION

Provided are pharmaceutical compositions and methods for preparing pharmaceutical compositions that are formulated to preserve the functional coating of a functionally-coated API particle during the manufacture process. Functionally-coated API particles are often mixed into a solution or suspension to form a pharmaceutical suspension. A pharmaceutical suspension allows for accurate dosing to form an administrable pharmaceutical product (i.e, pharmaceutical composition). Typically, shear forces required to incorporate the functionally-coated API particles into a suspension can cause the functional coating to erode. Erosion of this coating can destroy or damage the properties of the functional coating. Accordingly, functionally-coated API particles with an eroded coating can experience an increased dissolution rate and decreased taste-masking properties when orally administered to a patient.

However, pharmaceutical compositions and methods for preparing pharmaceutical compositions provided herein include preserving the coating of functionally-coated API particles in a pharmaceutical suspension with hydrophobic fumed silica. Specifically, the hydrophobic fumed silica can provide a protective layer surrounding and/or embedded into the functionally-coated API particle. In some embodiments, solventless processes for producing functionally-coated API particles may produce APIs comprising a first coating. According to some embodiments, hydrophobic fumed silica can be added during the solventless mixing process to produce a second, protective coating surrounding and/or partially or fully embedded into the functionally-coated API particles.

Additionally, the second, protective coating may limit the interaction between the functionally-coated API and the matrix solution/suspension such that impact of the functionally-coated API on the performance characteristics of the matrix is minimized.

In some embodiments, a pharmaceutical composition is provided, the pharmaceutical composition comprising an API particle; a first coating comprising one or more deformed components coating the API particle; a second coating comprising silica on top of the first coating; a matrix former; and a structure former. In some embodiments of the pharmaceutical composition, the first coating is configured to mask a taste of the API particle. In some embodiments, the pharmaceutical composition comprises 10-30 wt. % the first coating and 0.5-10 wt. % the second coating. In some embodiments, the pharmaceutical composition comprises 3-15 wt. % or 4-10 wt. % the structure former and/or 3-15 wt. % or 4-10 wt. % the matrix former. In some embodiments of the pharmaceutical composition, the one or more deformed components of the first coating comprises a wax. In some embodiments of the pharmaceutical composition, the wax comprises one or more of carnauba wax, candelilla wax, or synthetic wax. In some embodiments of the pharmaceutical composition, the matrix former comprises one or more of a water soluble material, a water dispersible material, a polypeptide, a polysaccharide, polyvinyl alcohol, polyvinylpyrrolidone, and acacia. In some embodiments of the pharmaceutical composition, the matrix former comprises a polypeptide. In some embodiments of the pharmaceutical composition, the matrix former comprises gelatin. In some embodiments of the pharmaceutical composition, the structure former comprises one or more of mannitol, dextrose, lactose, galactose, and cyclodextrin. In some embodiments of the pharmaceutical composition, the structure former comprises mannitol.

In some embodiments, a pharmaceutical composition is provided, the pharmaceutical composition comprising coated API particles comprising: an API particle; a first coating comprising one or more deformed components; and a second coating comprising silica; a matrix former; and a structure former, wherein the pharmaceutical composition is prepared by mixing the coated API particles into a matrix solution/suspension comprising the matrix former and the structure former and a solvent to form a pharmaceutical suspension, and dosing the pharmaceutical suspension comprising the coated API particles into molds. In some embodiments of the pharmaceutical composition, the first coating is configured to mask a taste of the API particle. In some embodiments of the pharmaceutical composition, the one or more deformed components of the first coating material comprises a wax. In some embodiments of the pharmaceutical composition, the wax comprises one or more of carnauba wax, candelilla wax, or synthetic wax. In some embodiments of the pharmaceutical composition, the matrix former comprises one or more of a water soluble material, a water dispersible material, a polypeptide, a polysaccharide, polyvinyl alcohol, polyvinylpyrrolidone, and acacia. In some embodiments of the pharmaceutical composition, the matrix former comprises a polypeptide. In some embodiments of the pharmaceutical composition, the matrix former comprises gelatin. In some embodiments of the pharmaceutical composition, the structure former comprises one or more of mannitol, dextrose, lactose, galactose, and cyclodextrin. In some embodiments of the pharmaceutical composition, the structure former comprises mannitol.

In some embodiments, a method of preparing a pharmaceutical composition is provided, the method comprising: combining API particles with particles of a first coating material, wherein the first coating material comprises one or more deformable components; applying energy to the combination of API particles and the particles of the first coating material to form an ordered mixture of API particles comprising a discrete layer of the particles of the first coating material on a surface of the API particles; applying energy to the ordered mixture of API particles and particles of the first coating material to deform the one or more deformable components to form coated API particles, wherein the coated API particles comprise a continuous film of the first coating material surrounding each of the API particles; combining the coated API particles with particles of a second coating material to form coated API particles comprising a second coating; and mixing the coated API particles comprising a second coating into a matrix solution/suspension to form a pharmaceutical suspension. In some embodiments of the method, the first coating material is configured to mask a taste of the API particle. In some embodiments of the method, the methods comprises dosing the suspension into preformed molds. In some embodiments of the method, the one or more deformable components of the first coating material comprises a wax. In some embodiments of the method, the wax comprises one or more of carnauba wax, candelilla wax, or synthetic wax. In some embodiments of the method, the second coating material comprises silica. In some embodiments of the method, the matrix solution/suspension comprises a matrix former and a structure former. In some embodiments of the method, the matrix former comprises one or more of a water soluble material, a water dispersible material, a polypeptide, a polysaccharide, polyvinyl alcohol, polyvinylpyrrolidone, and acacia. In some embodiments of the method, the matrix former comprises a polypeptide. In some embodiments of the method, the matrix former comprises gelatin. In some embodiments of the method, the structure former comprises one or more of mannitol, dextrose, lactose, galactose, and cyclodextrin. In some embodiments of the method, the structure former comprises mannitol.

BRIEF DESCRIPTION OF THE DRAWINGS

The invention will now be described, by way of example only, with reference to the accompanying drawings, in which:

FIG. 1A shows an API particle functionally-coated with particles of deformable coating material according to some embodiments;

FIG. 1B shows an API particle functionally-coated with a continuous film layer of deformable coating material (i.e., a first functional coating) according to some embodiments;

FIG. 1C shows an API particle functionally-coated with a continuous film layer of deformable coating material (i.e., a first functional coating) with particles of a second coating material surrounding and/or partially embedded and/or embedded in the surface of the continuous film layer (i.e., a second protective coating) according to some embodiments;

FIG. 2 shows a scanning electron microscope (SEM) image of an un-coated API particle;

DETAILED DESCRIPTION OF THE INVENTION

Figure 3:
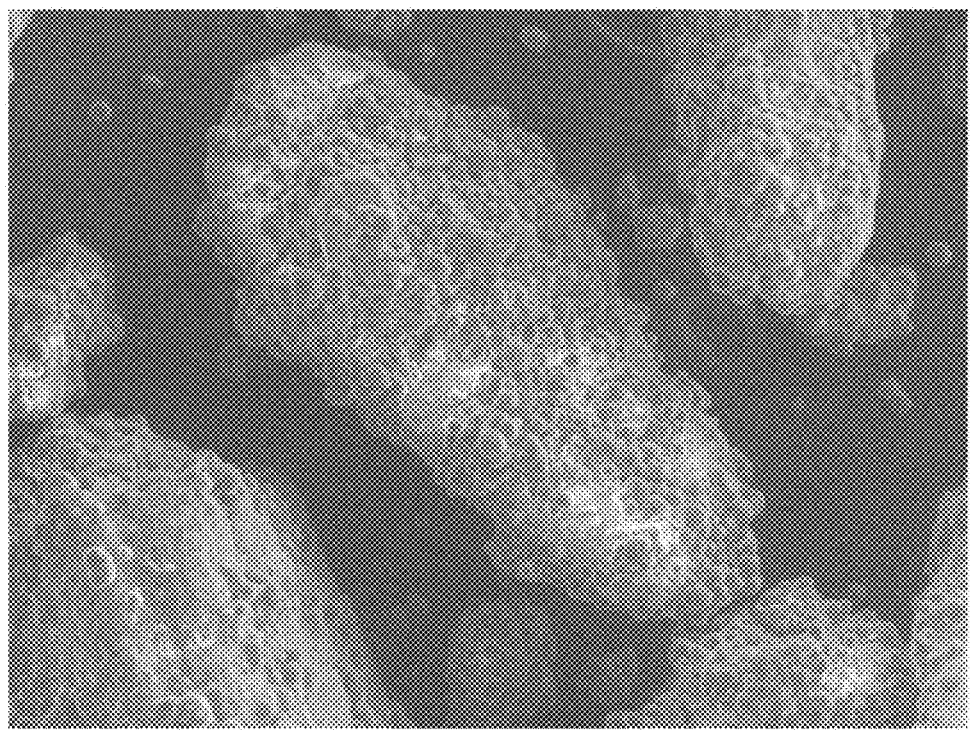
FIG. 3 shows an SEM image of a functionally-coated API particle according to some embodiments.

Described herein are exemplary embodiments of pharmaceutical compositions and methods for preparing pharmaceutical compositions formulated to preserve functionally-coated API particles produced by a dry, solventless mixing process and mixed in a matrix solution/suspension to form a pharmaceutical suspension. Specifically, pharmaceutical compositions and methods for preparing pharmaceutical compositions provided herein may include adding hydrophobic fumed silica during the coating process to provide a protective layer surrounding and/or partially or fully embedded into a functional (or "first coating") of the functionally-coated API particles. The addition of this hydrophobic fumed silica layer (or "second layer") can provide a protective layer to a first coating layer of functionally-coated API particles and can minimize erosion of the first coating layer from shear forces necessary to mix the functionally-coated API particles with a matrix solution/suspension.

Generally, a solventless mixing process for coating API particles includes mixing coating materials with API particles to produce functionally-coated API particles. The functionally-coated API particles are then stressed mechanically and/or thermally to deform the deformable coating material, creating a continuous film surrounding the API particles. The functionally-coated API particles are then placed into a matrix solution/suspension to form a pharmaceutical suspension. The pharmaceutical suspension comprising the functionally-coated API particles can be dosed into preformed molds, such as blister packs, and further treated to produce a dispensable pharmaceutical composition (e.g., a lyophilizate, a wafer, a tablet, etc.). In some embodiments, the dispensable pharmaceutical composition may be an orodispersible product. Ideally, a minimal amount, if any, of the API of the final dispensable pharmaceutical composition dissolves within the first few minutes of oral administration. This delay, or substantial reduction of API release, allows for the taste of the API to be masked when the orodispersible product is in a patient's mouth. Instead, the API can release once the pharmaceutical composition has passed to the gastrointestinal tract.

However, when the functionally-coated API particles are mixed with a matrix solution/suspension, the shear forces required to mix the particles into the matrix solution/suspension can erode the functional coating of the API particles. Erosion of the coating can destroy or damage the properties of the functional coating. For example, erosion of the functional coating can destroy or damage any taste-masking properties of the functional coating and allow the API to undergo dissolution in the oral cavity.

Accordingly, it has been discovered that hydrophobic fumed silica, as well as being used as a flow aid for the functionally-coated API to aid downstream processing, may also be used to provide a hydrophobic barrier layer surrounding and/or partially or fully embedded into the functionally-coated API particles. Specifically, the hydrophobic barrier layer formed by the hydrophobic fumed silica can protect one or more underlying coatings of the functionally-coated API particles during preparation of the pharmaceutical suspension and other downstream processing of the functionally-coated API particles. Thus, API particles according to some embodiments described herein may have a first, functional coating and a second, protective coating.

However, some pharmaceutical compositions and methods of preparing pharmaceutical compositions provided herein may include more than a first coating and a second coating. For example, some pharmaceutical compositions and methods of preparing the same may include three, four, five, six, or more coatings. Thus, the terms "first coating" and "second coating" as used herein should not be construed narrowly. As used herein, the term "first coating" refers to a functional coating of an API particle, and "second coating" refers to a protective coating comprising silica. In some embodiments, a functionally-coated API may have one or more coating layers between a "first coating" and a "second coating". In some embodiments, a functionally-coated API may have one or more coating layers between the API and the "first coating". In some embodiments, a functionally-coated API may have one or more coating layers on top of a "second coating".

The compositions and methods of preparing pharmaceutical compositions provided herein can be applied to functionally-coated API particles produced using dry, solventless processes. For example, processes according to some embodiments may be designed particularly to produce pharmaceutical compositions comprising APIs with a poor taste that may be administered to pediatric patients, geriatric patients, animal patients, and/or other types of patients that may have difficulties swallowing or may be sensitive to taste. In particular, many APIs have an undesirable taste and/or a numbing effect that may be problematic for these patients. Accordingly, some mixing processes according to embodiments described herein include coating/encapsulating API particles with a taste-masking coating. Such coatings can control the dissolution rate of an orodispersible pharmaceutical composition such that the release of the API upon oral administration is delayed or significantly reduced during the first few minutes, yet a satisfactory amount of the API is released within 30 minutes from oral administration. (For example, a satisfactory amount of API may be 90% of the API amount which would be released without the coating). U.S. Pat. No. 9,107,851 (the '851 patent) is directed to an example dry, solventless process for coating pharmaceutical ingredients, the entirety of which is incorporated herein.

However, other variations of coating/encapsulating processes may be used as well. For example, sugar coating, film coating, other variations of microencapsulation, compression coating, other variations of dry coating, melting coating, dip coating, rotary die coating, electrostatic coating, and/or other suitable types of coating may be used in combination with the other processing steps for preparing pharmaceutical compositions formulated to presence functionally coated APIs provided herein.

FIGS. 1A, 1B, and 1C illustrate different phases of a functionally-coated API particle according to some embodiments. In some embodiments, API particles can be combined with one or more coating materials to produce functionally-coated API particles. This functional coating may comprise materials including a water soluble material, a water swellable material, and/or a water insoluble material (described in detail below).

For example, FIG. 1A shows an API particle 102 surrounded by particles of a coating material 104. To achieve the functionally-coated API particle of FIG. 1A, the combined API particles (i.e., API particle 102) and one or more coating material(s) (i.e., coating material particles 104) may be exposed to mechanical and/or thermal energy to produce an ordered mixture of API particles 102 comprising a discrete layer of coating material particles 104 layering the surface of the API particle 102. API particle 102 of FIG. 1A is shown with a single layer of discrete particles of coating material(s). However, API particle 102 may have two or more discrete layers of coating particles. Additionally, FIG. 2 shows an SEM image of an un-coated API particle.

FIG. 1B demonstrates API particle 102 surrounded by continuous, deformed film layer 104. Specifically, FIG. 1B shows that all of the coating material particles 104 may be deformable and may deform when subjected to mechanical stress and/or elevated temperature. Thus, because all the coating materials comprise deformable characteristics, the coating material 104 of FIG. 1B is a relatively smooth and continuous coating layer after exposure to mechanical and/or thermal energy. In some embodiments, API particle 102 may have two or more relatively smooth and continuous coating layers. "Continuous film" as used herein may be a layer surrounding an API particle formed by melting/softening or otherwise breaking down one or more deformable components of the individual coating material particles such that they comprise a single, continuous layer surrounding the API particle. FIG. 3 also provides an SEM image showing a functionally-coated API particle according to some embodiments.

In some embodiments, one or more of the coating materials may not be deformable but may be embedded in the deformable coating layer. Thus, the continuous film may comprise solid particles of the non-deformable material embedded within the deformed coating material. FIG. 1C shows that continuous film 104 may comprise solid non-deformable particles 108 of one or more non-deformable materials surrounding and/or partially embedded and/or embedded within the deformed coating material of continuous film 104. This continuous film 104 of FIG. 1B or 1C can ensure a functional coating (for example, a coating that masks the taste of the API) and a delayed API release. In some embodiments, API particle 102 may have two or more continuous coating layers surrounded by and/or partially embedded and/or embedded with non-deformable coating material particles. FIG. 3 also provides an SEM image showing a functionally-coated API particle according to some embodiments.

As used herein, the terms "deformable", "deformable components", "deformable components of the coating material" and other related terms refer to one or more components of the water soluble, water swellable, and/or water insoluble materials that can be broken down when subjected to mechanical stress and/or elevated temperature.

API particle 102 of the functionally-coated API particles may be any of numerous APIs. FIG. 2 shows an SEM image of an un-coated API particle according to some embodiments. As used herein, "active pharmaceutical ingredient" or "API" refers to a drug product that may be used in the diagnosis, cure, mitigation, treatment, or prevention of disease. Any API may be used for purposes of the present disclosure. Suitable APIs include, without limitation: analgesics and anti-inflammatory agents, antacids, anthelmintics, anti-arrhythnic agents, anti-bacterial agents, anti-coagulants, anti-depressants, anti-diabetics, anti-diarrheals, anti-epileptics, anti-fungal agents, anti-gout agents, antihypertensive agents, anti-malarials, anti-migraine agents, anti-muscarinic agents, anti-neoplastic agents and immunosuppressants, anti-protazoal agents, antirheumatics, anti-thyroid agents, antivirals, anxiolytics, sedatives, hypnotics and neuroleptics, beta-blockers, cardiac inotropic agents, corticosteroids, cough suppressants, cytotoxics, decongestants, diuretics, enzymes, anti-parkinsonian agents, gastro-intestinal agents, histamine receptor antagonists, lipid regulating agents, local anesthetics, neuromuscular agents, nitrates and anti-anginal agents, nutritional agents, opioid analgesics, oral vaccines, proteins, peptides and recombinant drugs, sex hormones and contraceptives, spermicides, and stimulants; and combinations thereof. A list of specific examples of these API may be found in U.S. Pat. No. 6,709,669, which is incorporated herein by reference. When present, the API is present in the pharmaceutical formulation in an amount that is necessary to exhibit the required physiological effect as established by clinical studies. One of ordinary skill in the art can readily determine an appropriate amount of API to include in the dosage form made according to the present disclosure.

In some embodiments, the functionally-coated API particles or pharmaceutical composition may comprise from 30.0 to 90.0% w/w API. In some embodiments, the functionally-coated API particles or pharmaceutical composition may comprise from 40.0 to 85.0% w/w, from 50.0 to 80.0% w/w, or from 70.0 to 80.0% w/w API. In some embodiments, the functionally-coated API particles or pharmaceutical composition may comprise more than 40.0% w/w, more than 50.0% w/w, more than 60.0% w/w, more than 65% w/w, more than 70.0% w/w, more than 75.0% w/w, more than 80.0% w/w, or more than 85.0% w/w API. In some embodiments, the functionally-coated API composition or pharmaceutical composition may comprise less than 90.0% w/w, less than 85.0% w/w, less than 80.0% w/w, less than 75.0% w/w, less than 70.0% w/w, less than 60.0% w/w, less than 50.0% w/w, or less than 40.0% w/w API.

The functional coating 104 surrounding the API particle 102 may comprise materials including a water soluble material, a water swellable material, and/or a water insoluble material. In some embodiments, this first, functional coating may coat an API particle directly, or it may coat an API particle already comprising one or more coatings.

The water swellable material of the first coating material may be a particle comprising a median particle size of about 0.5 µm to about 20 µm or about 1 µm to about 10 µm. In some embodiments, the water swellable material may be approximately ten times smaller than that of the API to enable ordered mixing and coating. The water swellable material can swell upon absorption of water such that a diameter of the water swellable particle increases at least by about 120-600%. The coating material or pharmaceutical composition may comprise from 0 to 8% w/w or from 0.1 to 0.9% w/w water swellable materials. In some embodiments, the coating material or pharmaceutical composition may comprise from 0.5 to 6.0% w/w, from 1.0 to 4.0% w/w, from 1.5 to 3.5% w/w, or from 2.0 to 3.0% w/w water swellable materials. In some embodiments, the coating material or pharmaceutical composition may comprise less than 8.0% w/w, less than 6.0% w/w, less than 4.0% w/w, less than 2.0% w/w, less than 1.0% w/w, or less than 0.5% w/w water swellable materials. In some embodiments, the coating material or pharmaceutical composition may comprise greater than 0.1% w/w, greater than 0.5% w/w, greater than 1.0% w/w, greater than 2.0% w/w, greater than 3.0 w/w %, greater than 5.0% w/w, or greater than 6.0% w/w water swellable materials. The water swellable material of the coating material may be deformable under mechanical stress and/or elevated temperature (described in detail below). The water swellable material may be any one or more of crospovidone, croscarmellose, sodium starch glycolate, or any other suitable disintegrant used in the pharmaceutical industry as an additive or blend made for tableting.

The water soluble material of the coating material may also be a particle comprising a median particle size of about 0.5 µm to about 20 µm or about 1 µm to about 10 µm. In some embodiments, the water soluble material may be approximately ten times smaller than that of the API to enable ordered mixing and coating. The water soluble material may have a water solubility of at least about 50 mg/ml in water at a neutral pH and at 20° C. Further, the water soluble material can have an intrinsic dissolution rate of about 3-60 µg/m$^2$ s. The water soluble material of the coating material may be deformable under mechanical energy and/or thermal energy. The coating material or pharmaceutical composition may comprise from 0 to 35% w/w water soluble materials. In some embodiments, the coating material or pharmaceutical composition may comprise from 0.5 to 25% w/w, from 1.0 to 15% w/w, from 1.5 to 10% w/w, or from 2.0 to 3.0% w/w water soluble materials. In some embodiments, the coating material or pharmaceutical composition may comprise less than 35% w/w, less than 30% w/w, less than 25% w/w, less than 20% w/w, less than 15% w/w, less than 10% w/w, less than 5.0% w/w, less than 4.5% w/w, less than 4.0% w/w, less than 3.5% w/w, less than 3.0% w/w, less than 2.5% w/w, less than 2.0% w/w, less than 1.5% w/w, less than 1.0% w/w, or less than 0.5% w/w water soluble materials. In some embodiments, the coating material or pharmaceutical composition may comprise more than 0.1% w/w, more than 0.5% w/w, more than 1.0% w/w, more than 1.5% w/w, more than 2.0% w/w, more than 2.5% w/w, more than 3.0% w/w, more than 4.0% w/w, more than 5.0% w/w, more than 8.0% w/w, more than 10% w/w, more than 15% w/w, more than 20% w/w, more than 25% w/w, or more than 30% w/w water soluble materials. The water soluble material may be one or more of sucrose, mannitol, sorbitol, polyvinylpyrrolidone, hydroxypropylcellulose, lactose, poly-(ethylene oxide), and any other suitable micronizable materials or polyols.

The water insoluble material of the coating materials may also be a particle comprising an average particle size less than that of the API. In some embodiments, the water insoluble material may be approximately ten times smaller than that of the API to enable ordered mixing and coating. For example, the water insoluble material(s) may comprise an average particle size from about 1-20 µm, about 1-12 µm, about 2-10 µm, about 5-12 µm, or about 5-6 µm. The water insoluble material of the coating material may be deformable under mechanical stress and/or elevated temperature. The coating material or pharmaceutical composition may comprise from 5 to 70% w/w, from 10 to 60% w/w, from 10 to 50% w/w, from 10 to 40% w/w, from 10 to 35% w/w, or from 15 to 30% w/w water insoluble materials. In some embodiments, the coating material or pharmaceutical composition may comprise more than 5% w/w, more than 10% w/w, more than 15% w/w, more than 20% w/w, more than 25% w/w, more than 30% w/w, more than 35% w/w, or more than 40% w/w water insoluble materials. In some embodiments, the coating material or pharmaceutical composition may comprise less than 70% w/w, less than 60% w/w, less than 50% w/w, less than 45% w/w, less than 40% w/w, less than 35% w/w, or less than 30% w/w water insoluble materials. Examples of suitable water insoluble materials include, but are not limited to ethylcellulose, polyethylene, polypropylene, polytetrafluoroethylene, carnauba wax, castor wax, candelilla wax, polyamide wax, and/or synthetic wax.

In some embodiments, mechanical and/or thermal energy may be used to deform the one or more water soluble materials, water swellable materials, and/or water insoluble materials. For example, mechanical stress can be applied to the functionally-coated API particles using a PharmaRAM II acoustic mixer. The functionally-coated API particles may be exposed to up to 100 times the force of gravity (100G acceleration) during this acoustic mixing process. These high forces cause particle-particle collisions that generate energy in the form of heat, which may be used to deform the one or more water soluble materials, water swellable materials, and/or water insoluble materials onto the API.

Once the functionally-coated API particles are prepared, they can be mixed into a matrix solution/suspension to prepare a pharmaceutical suspension for dosing. Mixing functionally-coated API particles into a matrix solution/suspension can erode the functional coating of the functionally-coated API particles. In some embodiments, to minimize this erosion, hydrophobic fumed silica can be used to form a second coating layer surrounding and/or partially embedded and/or embedded into the functionally-coated API particles.

However, coating functionally-coated API particles (i.e., API particles comprising at least a first coating, as described above) that will later be mixed into a matrix solution/suspension with hydrophobic fumed silica is not naturally intuitive. As described above, to create an orodispersible pharmaceutical composition according to embodiments described herein, the functionally-coated API particles are mixed into a matrix solution/suspension comprising a matrix former, a structure former, and a solvent (often water). However, a hydrophobic material is naturally resistant to mixing into a matrix solution/suspension. Accordingly, one might assume that hydrophobic fumed silica would increase the interfacial tension between the functionally-coated API particles and the matrix solution/suspension, increasing the difficulty of incorporating the functionally-coated API particles into the matrix solution/suspension and potentially causing phase separation of the pharmaceutical suspension.

Interestingly, it has been determined that hydrophobic fumed silica can be used to coat functionally-coated API particles comprising to preserve the first, functional coating without substantially interfering with the incorporation of the functionally-coated API particles into the matrix solution/suspension. As described above, a hydrophobic material in an matrix solution/suspension, such as the functionally-coated API particles covered with the hydrophobic fumed silica in the matrix solution/suspension described above, characteristically exhibits a relatively high surface tension between the hydrophobic material and the matrix solution/suspension. Accordingly, the surface tension between the hydrophobic functionally-coated API particles and the matrix solution/suspension is likely relatively high as well.

However, as discussed below, the matrix solution/suspension may comprise a matrix former such as gelatin. Some matrix formers, including gelatin, are mild surfactants, meaning that they can lower the surface tension between two materials. Accordingly, it is believed that matrix formers exhibiting surfactant-like behaviors can reduce the surface tension between the functionally-coated API particles and the matrix solution/suspension, which in turn allows for incorporation of the functionally-coated API particles into the matrix solution/suspension, while at the same time maintaining the protective properties of the hydrophobic fumed silica coating layer with respect to the first, functional coating of the functionally-coated API particles. This second coating layer comprising hydrophobic fumed silica can provide a hydrophobic barrier to the underlying first coating of the functionally-coated API particles, to protect the underlying first coating from the shear forces required to mix the functionally-coated API particles into suspension. By coating the functionally-coated API particles with a hydrophobic barrier comprising hydrophobic fumed silica, the underlying (first) coating may be protected from erosion. Further, using hydrophobic fumed silica according to described methods can prevent the matrix solution/suspension from penetrating through the coating to the API particles.

Under normal processing conditions, without a hydrophobic fumed silica coating layer, the coating of the functionally-coated API particles can erode over time under the shear forces required to mix the functionally-coated API particles into the matrix solution/suspension. However, there can be a "processing window" of two or more hours from the time the functionally-coated API particles are first mixed into suspension wherein the coating can remain intact and its functionality can remain uncompromised. The exact time of this "processing window" varies and can depend upon the composition of the various components of the functionally-coated API particles, the composition of the matrix solution/suspension, the amount of material used to prepare the coating of the functionally-coated API particles, and/or the physicochemical properties of the API. However, with functionally-coated API particles having a second coating comprising fumed silica, this "processing window" can be extended.

In some embodiments, the pharmaceutical composition or the coated API can comprise from 0.5 to 35% w/w hydrophobic fumed silica. In some embodiments, the pharmaceutical composition or the coated API can comprise from 0.5 to 20% w/w, from 0.5 to 10% w/w, or from 0.5 to 5% w/w hydrophobic fumed silica. In some embodiments, the pharmaceutical composition or the coated API can comprise more than 0.5% w/w, more than 1.0% w/w, more than 1.5% w/w, more than 2.0% w/w, more than 2.5% w/w, more than 3.0% w/w, more than 4.0% w/w, more than 5.0% w/w, more than 10% w/w, more than 15% w/w, more than 20% w/w, more than 25% w/w, or more than 30% w/w hydrophobic fumed silica. In some embodiments the pharmaceutical composition or the coated API can comprise less than 35% w/w, less than 25% w/w, less than 15% w/w, less than 10% w/w, less than 5.0% w/w, less than 4.0% w/w, less than 3.5% w/w, less than 3.0% w/w, less than 2.5% w/w, less than 2.0% w/w, less than 1.5% w/w, or less than 1.0% w/w hydrophobic fumed silica. The hydrophobic fumed silica may be any of Aerosil R972 silica (Degussa), CAB-O-SIL EH-5 silica (Cabot), OX-50 silica (Degussa), COSM055 (Catalyst & Chemical Ind. Co. Ltd (Japan)), TS5 silica (Cabot), and/or other suitable types of silica.

Figure 4:
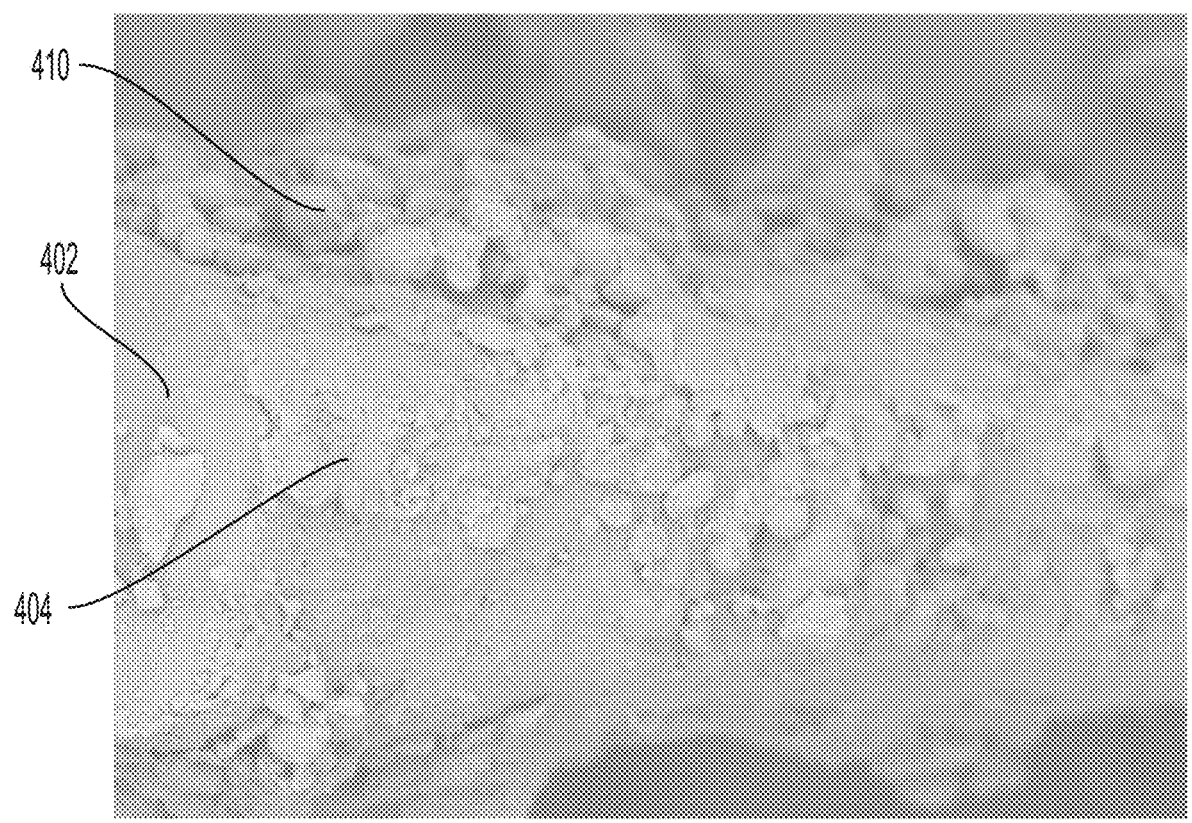
FIG. 4 shows an SEM image of a functionally-coated API particle comprising a second protective coating of hydrophobic fumed silica according to some embodiments.

FIG. 4 provides an SEM image of a functionally-coated API particle comprising an API 402, a first, functional coating 404, and a second, protective silica coating 410. As shown in the figure, the second, protective silica coating may be at least partially embedded into the first functional coating 404 of the functionally-coated API.

Once the silica is added to the functionally-coated API particles to prepare functionally-coated API particles, mechanical and/or thermal energy can be applied to the particles to form functionally-coated API particles comprising a protective silica coating. The functionally-coated API particles comprising a second, protective silica coating may then be prepared, added to a create a pharmaceutical suspension, and dosed to form an orodispersible pharmaceutical composition.

Some methods of preparing pharmaceutical compositions include using a mold to form the article (i.e., a pill or a tablet) and transferring the molded article to an air-tight container for storage. However, using blister packs can reduce this transferring step and save time, money, and associated risks (i.e., damage, loss, contamination, etc.). Thus, methods according to some embodiments provided herein can include dosing the pharmaceutical suspension into blister packs, freeze-drying the suspension to remove the solvent, and sealing the pharmaceutical compositions in the blister packs for protection. This pharmaceutical suspension and dosing process is covered in detail in GB 1548022, U.S. Pat. Nos. 4,371,516, 4,305,502, GB 211423, and U.S. Pat. No. 4,758,598, each of which is incorporated herein in its entirety.

The functionally-coated API particles can be placed into a matrix solution/suspension to form a pharmaceutical suspension that may be dosed into preformed blister packs, frozen, and freeze-dried to produce orally-disintegrating tablets (i.e., pharmaceutical compositions).

The matrix solution/suspension may include a matrix former, a structure former, a viscosity modifier, and/or a solvent. For example, the matrix former may include any water soluble or water dispersable material that is pharmacologically acceptable or inert to the functionally-coated API particles. In some embodiments, the matrix former may be a polypeptide such as gelatin. The gelatin may be at least partially hydrolyzed (by heating in water). Other suitable matrix former materials include, but are not limited to, polysaccharides such as hydrolyzed dextran, dextrin, and alginates, polyvinyl alcohol, polyvinylpyrrolidone, and/or acacia. In some embodiments, the amount of matrix former in a matrix solution/suspension or pharmaceutical suspension can be from about 0.1 to 10% w/w. In some embodiments, the amount of matrix former in the matrix solution/suspension or pharmaceutical suspension may include from 1.0 to 8.0% w/w or from 2.0 to 5.0% w/w. In some embodiments, the amount of matrix former in the matrix solution/suspension or pharmaceutical suspension may include more than 0.1% w/w, more than 0.5% w/w, more than 1.0% w/w, more than 2.0% w/w, more than 3.0% w/w, more than 4.0% w/w, more than 4.0% w/w, more than 5.0% w/w, or more than 8.0% w/w. In some embodiments, the amount of matrix former in the matrix solution/suspension or pharmaceutical suspension may include less than 10% w/w, less than 8.0% w/w, less than 6.0% w/w, less than 5.0% w/w, less than 4.0% w/w, less than 3.0% w/w, less than 2.5% w/w, less than 2.0% w/w, less than 1.5% w/w, or less than 1.0% w/w. In some embodiments, the amount of matrix former in a pharmaceutical composition can be about 3-15% w/w, about 4-10% w/w, or about 4-7% w/w. In some embodiments, the amount of matrix former in the pharmaceutical composition may include more than 0.1% w/w, more than 0.5% w/w, more than 1.0% w/w, more than 2.0% w/w, more than 3.0% w/w, more than 4.0% w/w, more than 5.0% w/w, more than 6.0% w/w, more than 7.0% w/w, more than 8.0% w/w, more than 9.0% w/w, more than 10.0% w/w, more than 11.0% w/w, more than 12.0% w/w, more than 13.0% w/w, or more than 14.0% w/w. In some embodiments, the amount of matrix former in the pharmaceutical composition may include less than 15% w/w, less than 14.0% w/w, less than 13.0% w/w, less than 12.0% w/w, less than 10.0% w/w, less than 9.0% w/w, less than 8% w/w, less than 7% w/w, less than 6% w/w, less than 5% w/w, or less than 4.0% w/w.

A structure former, or bulking agent, of the matrix solution/suspension may include a sugar. For example, suitable structure formers include, but are not limited to, mannitol, dextrose, lactose, galactose, glycine, cyclodextrin, or combinations thereof. The structure former can be used in freeze drying as a bulking agent as it crystallizes to provide structural robustness to the freeze-dried dosage form. In some embodiments, the amount of structure former in the matrix solution/suspension or pharmaceutical suspension can be from about 0.1 to 10% w/w. In some embodiments, the amount of structure former in the matrix solution/suspension or pharmaceutical suspension may include from 1.0 to 8.0% w/w or from 2.0 to 5.0% w/w. In some embodiments, the amount of structure former in the matrix solution/suspension or pharmaceutical suspension may include more than 0.1% w/w, more than 0.5% w/w, more than 1.0% w/w, more than 2.0% w/w, more than 3.0% w/w, more than 4.0% w/w, more than 4.5% w/w, more than 5.0% w/w, or more than 8.0% w/w. In some embodiments, the amount of structure former in the matrix solution/suspension or pharmaceutical suspension may include less than 10% w/w, less than 8.0% w/w, less than 6.0% w/w, less than 5.0% w/w, less than 4.0% w/w, less than 3.0% w/w, less than 2.5% w/w, less than 2.0% w/w, less than 1.5% w/w, or less than 1.0% w/w. In some embodiments, the amount of structure former in a pharmaceutical composition can be about 3-15% w/w, about 4-10% w/w, or about 4-7% w/w. In some embodiments, the amount of structure former in the pharmaceutical composition may include more than 0.1% w/w, more than 0.5% w/w, more than 1.0% w/w, more than 2.0% w/w, more than 3.0% w/w, more than 4.0% w/w, more than 5.0% w/w, more than 6.0% w/w, more than 7.0% w/w, more than 8.0% w/w, more than 9.0% w/w, more than 10.0% w/w, more than 11.0% w/w, more than 12.0% w/w, more than 13.0% w/w, or more than 14.0% w/w. In some embodiments, the amount of structure former in the pharmaceutical composition may include less than 15% w/w, less than 14.0% w/w, less than 13.0% w/w, less than 12.0% w/w, less than 10.0% w/w, less than 9.0% w/w, less than 8% w/w, less than 7% w/w, less than 6% w/w, less than 5% w/w, or less than 4.0% w/w.

In some embodiments, a matrix solution/suspension and pharmaceutical suspension may include a viscosity modifier. For example, a viscosity modifier according to embodiments provided herein may include vegetable gums such as xanthan gum, alginin, guar gum, or locust bean gum, proteins such as collagen or gelatin, sugars such as agar, carboxymethyl cellulose, pectin, or carrageenan, starches such as arrowroot, cornstarch, katakuri starch, potato starch, sago, or tapioca, and/or other suitable viscosity modifiers. In some embodiments, the amount of viscosity modifier in the matrix solution/suspension, pharmaceutical suspension, or the pharmaceutical composition may be from 0 to 0.2% w/w or from 0.01 to 0.1% w/w. In some embodiments, the amount of viscosity modifier in the matrix solution/suspension, pharmaceutical suspension, or the pharmaceutical composition may be greater than 0.01% w/w, greater than 0.03% w/w, greater than 0.05% w/w, greater than 0.07% w/w, greater than 0.1% w/w, greater than 0.12% w/w, greater than 0.15% w/w, or greater than 0.17% w/w. In some embodiment, the amount of viscosity modifier in the matrix solution/suspension, pharmaceutical suspension, or the pharmaceutical composition may be less than 0.2% w/w, less than 0.18% w/w, less than 0.15% w/w, less than 0.12% w/w, less than 0.1% w/w, less than 0.08% w/w, less than 0.06% w/w, or less than 0.03% w/w.

The solvent of the matrix solution/suspension and pharmaceutical suspension may be water, but the matrix solution/suspension may include a cosolvent as well. In some embodiments, the solvent can be ethanol, alcohol, isopropanol, other lower alkanols, water (e.g., purified water), or combinations thereof. For example, a suitable solvent and/or cosolvent may be an alcohol, such as tert-butyl alcohol. In some embodiments, the balance remaining of the pharmaceutical formulation is the solvent (i.e., Q.S. 100%).

The matrix solution/suspension and pharmaceutical suspension may also contain additional pharmaceutically acceptable agents or excipients. Such additional pharmaceutically acceptable agents or excipients include, without limitation, sugars, inorganic salts, such as sodium chloride and aluminum silicates, modified starches, preservatives, antioxidants, coloring agents, flavoring agents, pH modifiers, sweeteners, taste-masking agents, and combinations thereof. Suitable coloring agents can include red, black and yellow iron oxides and FD & C dyes such as FD & C Blue No. 2 and FD & C Red No. 40, and combinations thereof. Suitable flavoring agents can include mint, raspberry, licorice, orange, lemon, grapefruit, caramel, vanilla, cherry and grape flavors and combinations of these. Suitable pH modifiers can include citric acid, tartaric acid, phosphoric acid, hydrochloric acid, maleic acid, sodium hydroxide (e.g., 3% w/w sodium hydroxide solution), and combinations thereof. Suitable sweeteners can include aspartame, acesulfame K and thaumatin, and combinations thereof. Suitable taste-masking agents can include sodium bicarbonate, ion-exchange resins, cyclodextrin inclusion compounds, adsorbates or microencapsulated actives, and combinations thereof. One of ordinary skill in the art can readily determine suitable amounts of these various additional excipients if desired.

Figure 5:
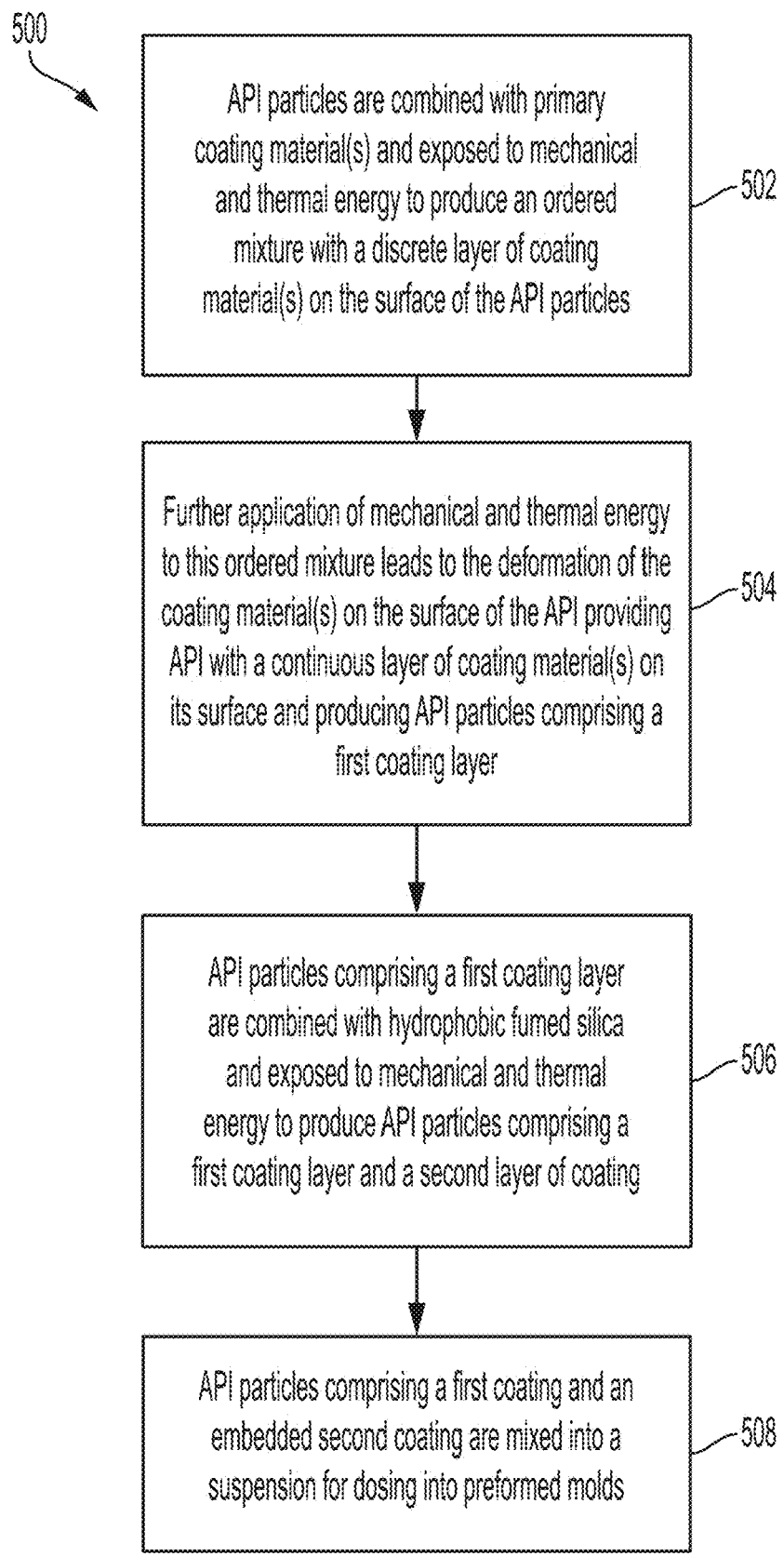
FIG. 5 is a flow chart demonstrating a method of producing functionally-coated API particles comprising a second protective coating of hydrophobic fumed silica according to some embodiments.

FIG. 5 provides a flow chart according to some embodiments of a mixing process for preparing pharmaceutical compositions described herein. In step 502, API particles are combined with one or more coating material(s), and the combination is exposed to mechanical and/or thermal energy to produce an ordered mixture of API particles comprising a discrete layer of one or more coating material(s) (i.e., API particles comprising a first coating layer). For example, FIG. 1A demonstrates an API particle comprising a discrete layer of coating material particles.

In step 504, mechanical and/or thermal energy may be applied to the functionally-coated API particles comprising a first coating to deform one or more deformable components of the coating material to the surface of the API particle. This process step can form API particles comprising a continuous film surrounding the API particles (i.e., functionally-coated API particles). This is shown in FIG. 1B, FIG. 1C, and/or FIG. 3.

In step 506, functionally-coated API particles are combined with hydrophobic fumed silica to form functionally-coated API particles comprising at least a first, functional coating and a second, protective silica coating. In some embodiments, mechanical and/or thermal energy may be applied to the combination of functionally-coated API particles and hydrophobic fumed silica to cause the hydrophobic fumed silica to adhere to and/or partially embed and/or embed into the coating of the functionally-coated API particles. For example, FIG. 4 shows an SEM image of an API particle 402 comprising a first coating 404 and an embedded silica coating 408.

In step 508, the API particles comprising a first coating with a second, hydrophobic fumed silica coating, are mixed into suspension for dosing into preformed molds. In some embodiments, the suspension may be dosed into blister packs, freeze-dried to remove the solvent, and sealed in the blister packs for protection. This suspension and dosing process is covered in detail in GB 1548022, U.S. Pat. Nos. 4,371,516, 4,305,502, GB 211423, and U.S. Pat. No. 4,758, 598, each of which is incorporated herein in its entirety.

The effectiveness of the hydrophobic fumed silica-comprising protective layer can be determined by measuring the particle size of the functionally-coated API particles in the pharmaceutical suspension over time. If the hydrophobic fumed silica is effective at preserving the coating, the particle size of the functionally-coated API particles can remain constant or decrease very little over time. If ineffective, the particle size of the functionally-coated API particles can decrease more substantially over time. The particle size of the functionally-coated particles can be measured using laser diffraction, a particle analyzer such as a Malvern Mastersizer, or any other suitable means for analyzing fine particles.

The effectiveness of the hydrophobic fumed silica-comprising protective layer can also be determined by conducting dissolution testing on the functionally-coated API particles. If the hydrophobic fumed silica is effective at preserving the coating, the release amount (e.g., percent of release) of the functionally-coated API particles over time will be slower in dissolution testing. If ineffective, the release amount of the functionally-coated API particles over time will be greater. The release amount of the functionally-coated particles can be measured using dissolution testing, a spectrophotometric analyzer such as a Pion MicroDISS Profiler, or any other suitable means for conducting dissolution testing.

Example 1: Hydrophobic fumed silica was used to coat functionally-coated API particles according to embodiments described herein. Specifically, the hydrophobic fumed silica that was used was Aerosil R972 ("Aerosil"). Two different concentrations of Aerosil R972 were tested-1.5% w/w and 1.0% % w/w. The size of the functionally-coated API particles were evaluated over a 6-hour holding period, during which they were subjected to low shear mixing.

Figure 6:
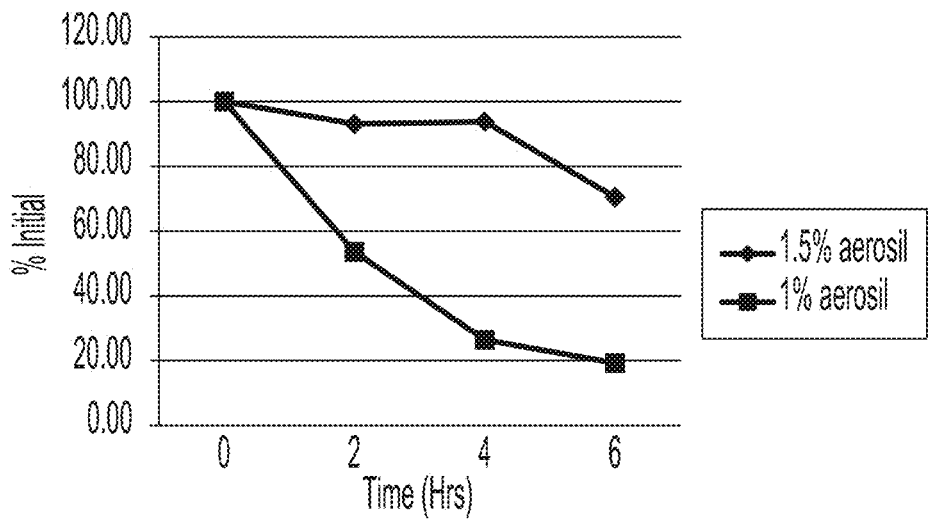
FIG. 6 is a graph providing an evaluation of d10 particle size of functionally-coated API comprising a second protective coating of different concentrations of silica, according to some embodiments.
Figure 7:
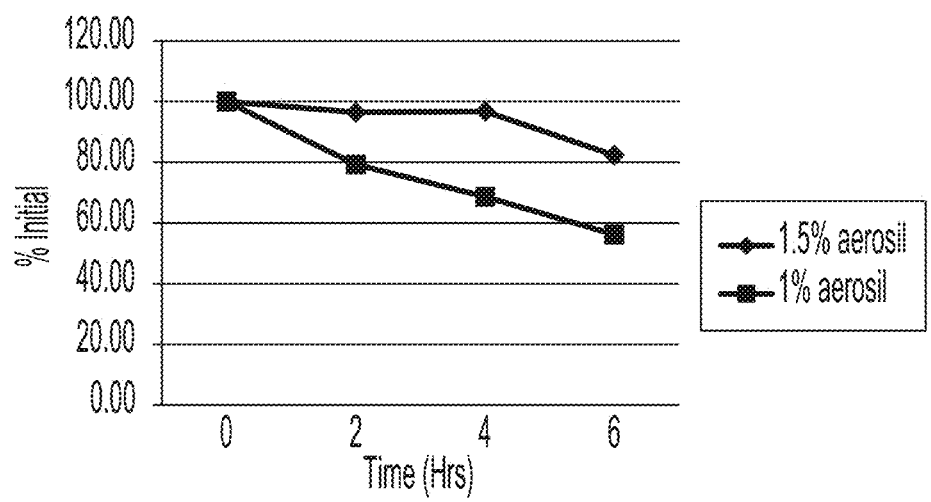
FIG. 7 shows a graph providing an evaluation of d50 particle size of functionally-coated API comprising a second protective coating of different concentrations of silica, according to some embodiments.
Figure 8:
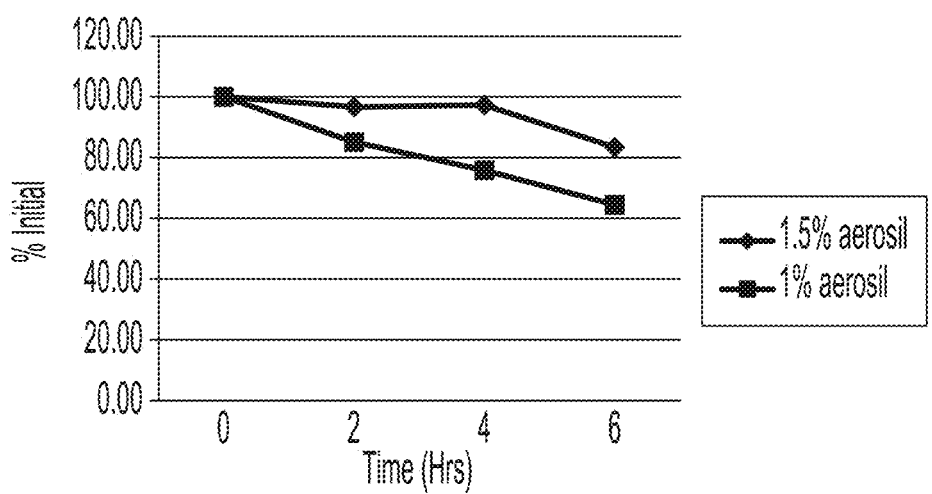
FIG. 8 shows a graph providing an evaluation of d90 particle size of functionally-coated API comprising a second protective coating of different concentrations of silica, according to some embodiments.

FIGS. 6, 7, and 8 provide evaluations of d10 particle size, d50 particle size, and d90 particle size, respectively, over a period of 6 hours. Generally speaking, a particle size expressed in terms of its d10 means that 10 percent of the particles in a given amount of sample lie below a given particle size. Accordingly, a particle size expressed in terms of its d50 means that 50 percent of the particles in a given amount of sample lie below a given particle size, and a particle size expressed in terms of its d90 means that 90 percent of the particles in a given amount of sample lie below a given particle size.

As shown in FIG. 6, the greater concentration of silica (1.5% w/w) was more effective at maintaining the original particle size, and thus maintaining the coating, than the lesser concentration of silica (1.0% w/w). Specifically, during the 6-hour period, the functionally-coated API particles comprising 1.5% w/w Aerosil lost approximately 30% of their original size, whereas the functionally-coated API particles comprising 1.0% w/w Aerosil lost approximately 80% of their original particle size.

FIG. 7 demonstrates that again the greater concentration of silica (1.5% w/w Aerosil) was more effective at maintaining the original functionally-coated API particle size, and thus preserving the functional coating, than the lesser concentration of silica (1.0% w/w Aerosil). Specifically, during a period of 6 hours, the functionally-functionally-coated API particles comprising 1.5% w/w Aerosil lost almost 20% of their original size, whereas the functionally-coated API particles comprising 1.0% w/w Aerosil lost approximately 45% of their original functionally-coated API particle size.

FIG. 8 also shows that the greater concentration of silica (1.5% w/w Aerosil) was more effective at maintaining the original functionally-coated API particle size, and thus preserving the functional coating of the functionally-coated API particles, than the lesser concentration of silica (1.0% w/w Aerosil). Specifically, during the 6-hour period, the functionally-coated API particles comprising 1.5% w/w Aerosil lost almost 15% of their original size, whereas the functionally-coated API particles comprising 1.0% w/w Aerosil lost approximately 35% of their original particle size.

Additionally, as the particle size of the functionally-coated API particles decreased, a separate population of particles comprising a particle size of 5 μm to 20 μm appeared and increased with time. These particles are believed to be non-deformable coating material particles embedded within the deformed, continuous coating material prior to erosion of the coating due to shear forces. Accordingly, as the coating erodes, and the particle size of the functionally-coated API particles decreases, the population size of these smaller particles increases as the deformed coating material surrounding them erodes, causing these non-deformable particles to release from the functionally-coated API particles.

Overall, these trials suggest that 1.5% w/w Aerosil coating the functionally-coated API particles may increase the "processing window" to approximately 4 hours, instead of the 2 hour "processing window" that exists without the silica. Within the first four hours of processing in suspension and comprising a second, outer coating comprising 1.5% w/w Aerosil, the functionally-coated API particles exhibit little, if any, erosion of the coating.

Example 2: Hydrophobic fumed silica was used to coat functionally-coated API particles according to embodiments described herein. Specifically, the hydrophobic fumed silica that was used was Aerosil R972 ("Aerosil"). Five different concentrations of Aerosil R972 were tested-0.0% w/w, 1.5% w/w, 2.5% w/w, 5.0% w/w and 10.0% w/w. The release amount of the functionally coated API particles was evaluated using dissolution testing (i.e., dissolution media of 0.01% SDS in pH 7.2 phosphate buffer, media temperature of 37° C., and media volume of 10 ml (Ibuprofen) or 20 ml (Paracetamol)).

Figure 9:
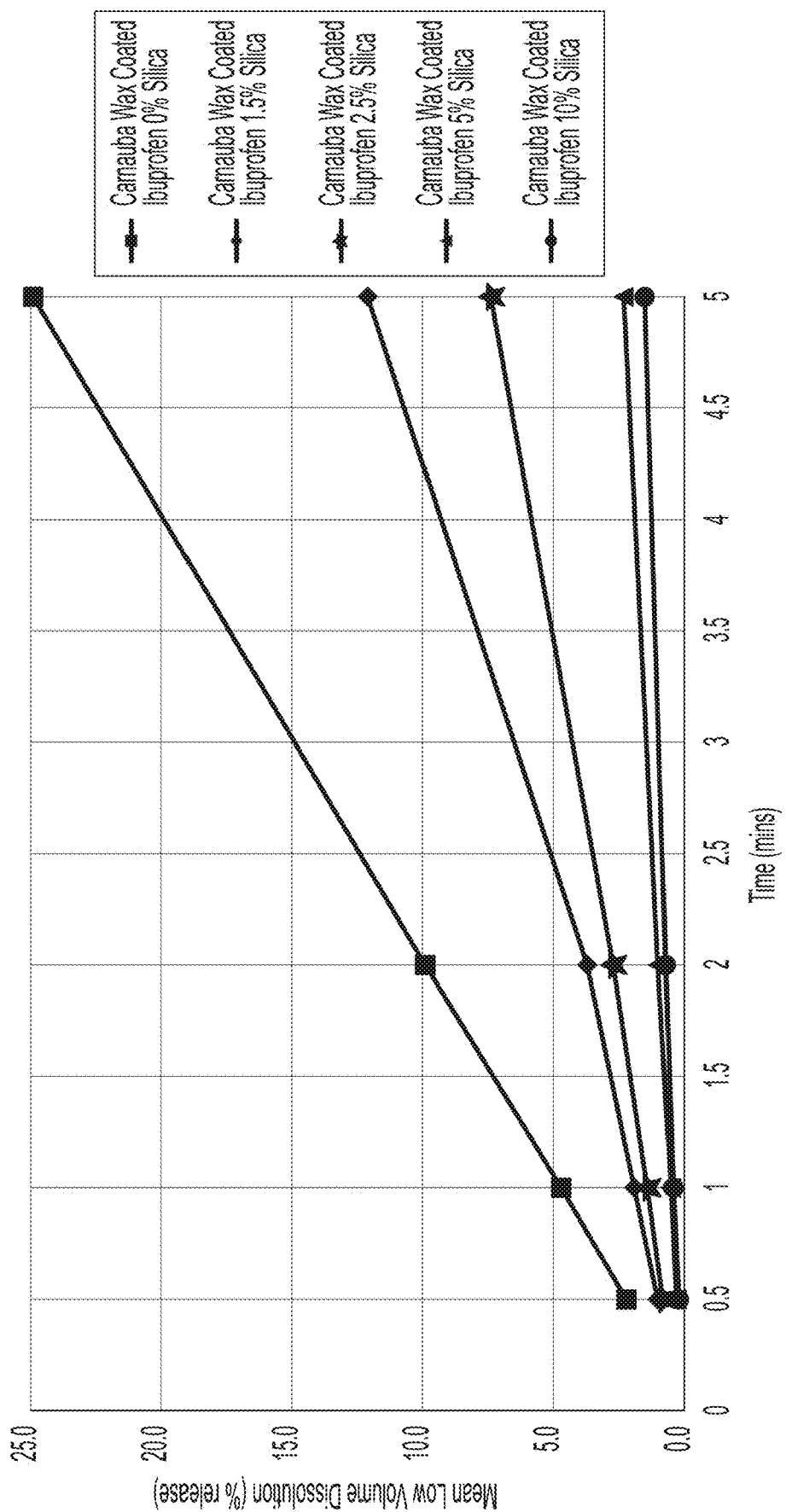
FIG. 9 shows a graph of low volume dissolution of Ibuprofen coated with carnauba wax with varying levels of hydrophobic fumed silica, according to some embodiments.
Figure 10:
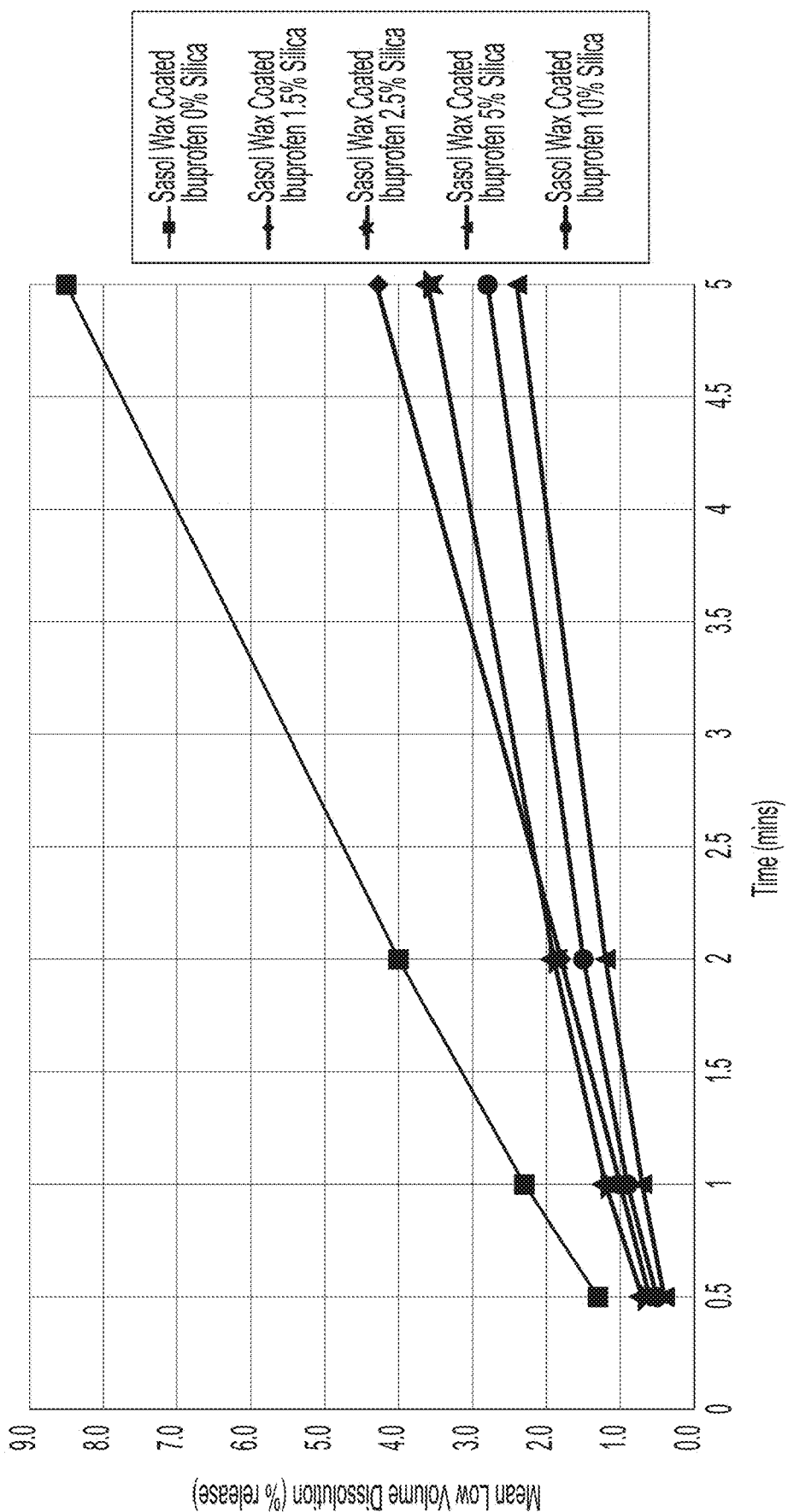
FIG. 10 shows a graph of low volume dissolution of Ibuprofen coated with Sasol (synthetic) wax comprising varying levels of hydrophobic fumed silica, according to some embodiments.
Figure 11:
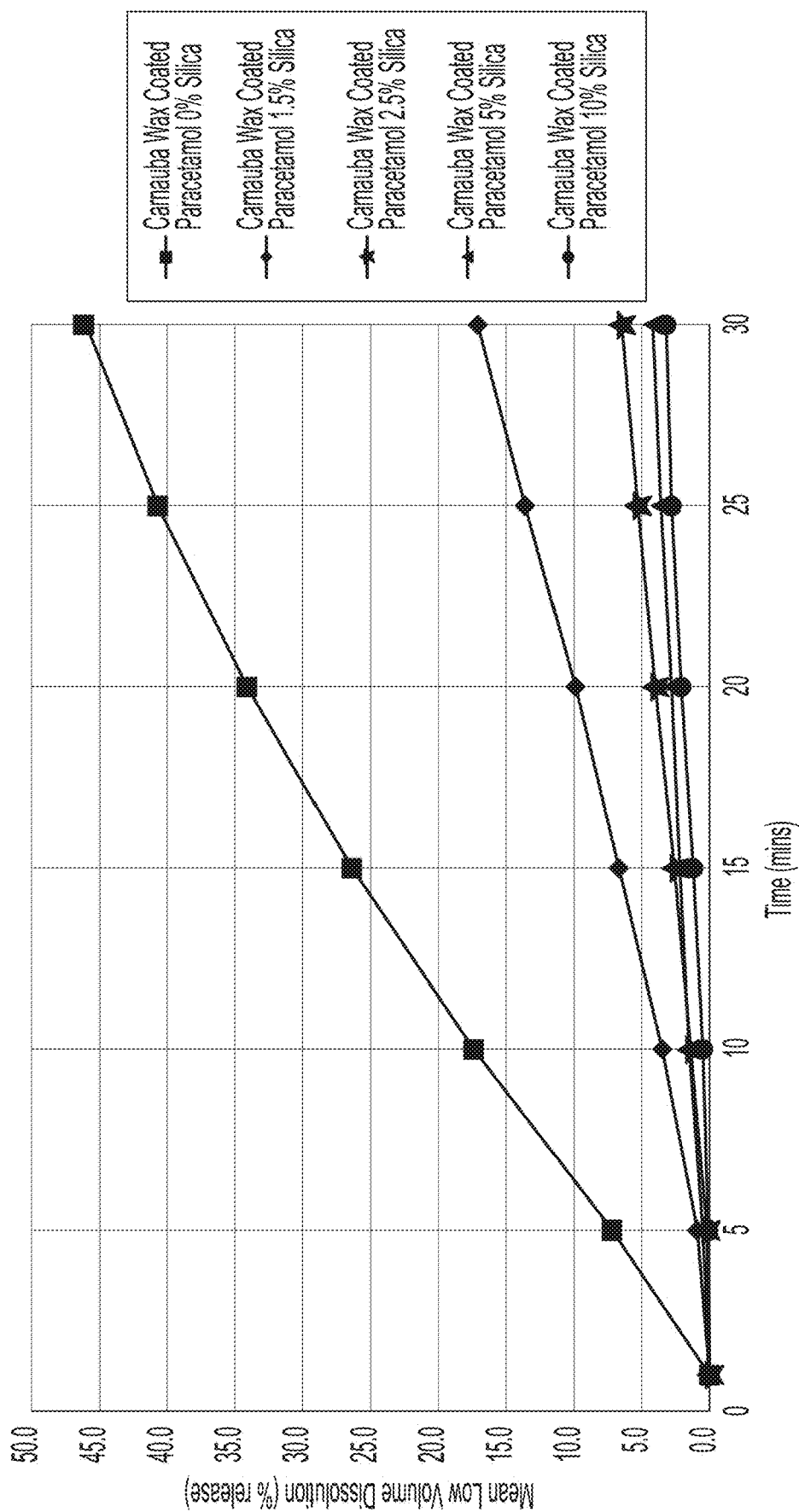
FIG. 11 shows a graph of low volume dissolution of Paracetamol coated with carnauba wax comprising varying levels of hydrophobic fumed silica, according to some embodiments.

FIGS. 9, 10, and 11 provide evaluations of release amount conducted on the functionally coated API particles, over a period of either 5 or 30 minutes. Generally speaking, a low volume dissolution result expressed in terms of its % release means that 'x' percent of the weight of material added has dissolved into solution.

FIG. 9 shows release data for Ibuprofen coated with carnauba wax and various amounts of hydrophobic silica. As shown in the Figure, greater concentrations of silica (up to 10.0% w/w) were more effective at providing a slower release rate in dissolution testing, and thus maintaining the coating, than the lesser concentrations of silica. Specifically, during the 5 minute testing period, the functionally-coated API particles (i.e., Ibuprofen coated with carnauba wax) comprising 10.0% w/w Aerosil exhibited a 1.5% release after 5 minutes, whereas the functionally-coated API particles comprising 0.0% w/w Aerosil exhibited a 24.9% release. Functionally-coated API particles comprising intermediate levels of Aerosil (i.e., 1.5% w/w, 2.5% w/w and 5.0% w/w) showed dissolution results after 5 minutes of 12.1% release, 7.4% release and 2.3% release, respectively.

FIG. 10 provides release data for Ibuprofen coated with Sasol (synthetic) wax and various levels of hydrophobic silica. FIG. 10 also shows that greater concentrations of silica (up to 10.0% w/w) were more effective at providing a slower release rate in dissolution testing, and thus maintaining the coating, than the lesser concentrations of silica. Specifically, during the 5 minute testing period, the functionally-coated API particles (i.e., Ibuprofen coated with synthetic wax) comprising 10.0% w/w Aerosil exhibited a 2.8% release after 5 minutes, whereas the functionally-coated API particles comprising 0.0% w/w Aerosil shows an 8.5% release. Functionally-coated API particles comprising intermediate levels of Aerosil (i.e., 1.5% w/w, 2.5% w/w and 5.0% w/w) gave dissolution results after 5 minutes of 4.3% release, 3.6% release and 2.4% release, respectively.

FIG. 11 provides release data for paracetamol coated with carnauba wax and various levels of hydrophobic silica. As with FIGS. 9 and 10, greater concentrations of silica (up to 10.0% w/w) were more effective at providing a slower release rate in dissolution testing, and thus maintaining the coating, than the lesser concentrations of silica. Specifically, during the 30 minute testing period, the functionally-coated API particles (i.e., paracetamol coated with carnauba wax) comprising 10.0% w/w Aerosil showed a 3.2% release after 30 minutes, whereas the functionally-coated API particles comprising 0.0% w/w Aerosil exhibited 46.0% release. Functionally-coated API particles comprising intermediate levels of Aerosil (i.e., 1.5% w/w, 2.5% w/w and 5.0% w/w) exhibited dissolution results after 30 minutes of 17.1% release, 6.5% release and 4.2% release, respectively.

Overall, these trials suggest that coating the functionally-coated API particles with Aerosil (up to 10% w/w) can increase the robustness of the coating for various API and coating materials. During dissolution testing, functionally-coated API particles comprising a second, outer protective coating of Aerosil particles exhibited less coating degradation than functionally-coated API particles that did not comprise a second, outer coating of Aerosil. Furthermore, the robustness of the functionally-coated API particles was found to increase with increasing levels of Aerosil (up to 10% w/w).

Unless defined otherwise, all terms of art, notations and other technical and scientific terms or terminology used herein are intended to have the same meaning as is commonly understood by one of ordinary skill in the art to which the claimed subject matter pertains. In some cases, terms with commonly understood meanings are defined herein for clarity and/or for ready reference, and the inclusion of such definitions herein should not necessarily be construed to represent a substantial difference over what is generally understood in the art.

Reference to "about" a value or parameter herein includes (and describes) variations that are directed to that value or parameter per se. For example, description referring to "about X" includes description of "X".

As used herein, the singular forms "a," "an," and "the" are intended to include the plural forms as well, unless the context clearly indicates otherwise. It is also to be understood that the term "and/or" as used herein refers to and encompasses any and all possible combinations of one or more of the associated listed items. It is further to be understood that the terms "includes, "including," "comprises," and/or "comprising," when used herein, specify the presence of stated features, integers, steps, operations, elements, components, and/or units but do not preclude the presence or addition of one or more other features, integers, steps, operations, elements, components, units, and/or groups thereof.

This application discloses several numerical ranges in the text and figures. The numerical ranges disclosed inherently support any range or value within the disclosed numerical ranges, including the endpoints, even though a precise range limitation is not stated verbatim in the specification because this disclosure can be practiced throughout the disclosed numerical ranges.

The foregoing description, for the purpose of explanation, has been described with reference to specific embodiments. However, the illustrative discussions above are not intended to be exhaustive or to limit the invention to the precise forms disclosed. Many modifications and variations are possible in view of the above teachings. The embodiments were chosen and described in order to best explain the principles of the techniques and their practical applications. Others skilled in the art are thereby enabled to best utilize the techniques and various embodiments with various modifications as are suited to the particular use contemplated.

Although the disclosure and examples have been fully described with reference to the accompanying figures, it is to be noted that various changes and modifications will become apparent to those skilled in the art. Such changes and modifications are to be understood as being included within the scope of the disclosure and examples as defined by the claims.

The invention claimed is:

1. A pharmaceutical composition comprising:
   a coated API particle comprising;
      a first coating comprising a wax; and
      a second coating comprising silica partially embedded in and/or embedded in the wax,
         wherein the coated API particle comprises 0.5-2.5% w/w silica and the silica produces a slower dissolution profile for the API as compared to API without silica.

2. The pharmaceutical composition of claim 1, wherein the first coating is configured to mask a taste of the API particle.

3. The pharmaceutical composition of claim 1, comprising a matrix former comprising one or more of a water soluble material, a water dispersible material, a polypeptide, a polysaccharide, polyvinyl alcohol, polyvinylpyrrolidone, and acacia.

4. The pharmaceutical composition of claim 3, wherein the matrix former comprises a polypeptide.

5. The pharmaceutical composition of claim 3, wherein the matrix former comprises gelatin.

6. The pharmaceutical composition of claim 1, comprising a structure former comprising one or more of mannitol, dextrose, lactose, galactose, and cyclodextrin.

7. The pharmaceutical composition of claim 6, wherein the structure former comprises mannitol.

8. The pharmaceutical composition of claim 1, wherein the wax comprises one or more of carnauba wax, candelilla wax, or synthetic wax.

9. A pharmaceutical composition comprising:
   coated API particles comprising:
      an API particle;
      a first coating comprising a wax; and
      a second coating comprising silica partially embedded in and/or embedded in the wax, wherein the coated API particle comprises 0.5-2.5% w/w silica and the silica produces a slower dissolution profile for the API as compared to API without silica,
wherein the pharmaceutical composition is prepared by mixing the coated API particles into a matrix solution/suspension to form a pharmaceutical suspension, and dosing the pharmaceutical suspension comprising the coated API particles into molds.

10. The pharmaceutical composition of claim 9, wherein the first coating is configured to mask a taste of the API particle.

11. The pharmaceutical composition of claim 9, comprising a matrix former comprising one or more of a water soluble material, a water dispersible material, a polypeptide, a polysaccharide, polyvinyl alcohol, polyvinylpyrrolidone, and acacia.

12. The pharmaceutical composition of claim 11, wherein the matrix former comprises a polypeptide.

13. The pharmaceutical composition of claim 11, wherein the matrix former comprises gelatin.

14. The pharmaceutical composition of claim 9, comprising a structure former comprising one or more of mannitol, dextrose, lactose, galactose, and cyclodextrin.

15. The pharmaceutical composition of claim 14, wherein the structure former comprises mannitol.

16. The pharmaceutical composition of claim 9, wherein the dosed pharmaceutical suspension comprising the coated API particle is frozen and freeze-dried to form a freeze-dried solid dosage form.

17. The pharmaceutical composition of claim 9, wherein the wax comprises one or more of carnauba wax, candelilla wax, or synthetic wax.

* * * * *